(12) United States Patent
Nakamura et al.

(10) Patent No.: US 8,772,259 B2
(45) Date of Patent: Jul. 8, 2014

(54) APTAMER TO FGF2 AND USE THEREOF

(75) Inventors: Yoshikazu Nakamura, Tokyo (JP); Akira Ishiguro, Tokyo (JP); Maiko Sakamoto, Tokyo (JP)

(73) Assignee: Ribomic Inc., Tokyo (JP)

( * ) Notice: Subject to any disclaimer, the term of this patent is extended or adjusted under 35 U.S.C. 154(b) by 0 days.

(21) Appl. No.: 13/578,023

(22) PCT Filed: Feb. 10, 2011

(86) PCT No.: PCT/JP2011/052925
§ 371 (c)(1),
(2), (4) Date: Oct. 31, 2012

(87) PCT Pub. No.: WO2011/099576
PCT Pub. Date: Aug. 18, 2011

(65) Prior Publication Data
US 2013/0039855 A1 Feb. 14, 2013

(30) Foreign Application Priority Data
Feb. 12, 2010 (JP) ................. 2010-029377

(51) Int. Cl.
*C12N 15/11* (2006.01)
*C12Q 1/68* (2006.01)
*C12N 15/115* (2010.01)

(52) U.S. Cl.
CPC .................... *C12N 15/115* (2013.01)
USPC .......................... 514/44 A; 435/6.1

(58) Field of Classification Search
None
See application file for complete search history.

(56) References Cited

U.S. PATENT DOCUMENTS

| 5,639,868 | A | 6/1997 | Janjic et al. |
| 6,759,392 | B1 | 7/2004 | Janjic et al. |

FOREIGN PATENT DOCUMENTS

| EP | 1 683 871 | 7/2006 |
| JP | 2008-206524 | 9/2008 |
| WO | 91/19813 | 12/1991 |
| WO | 94/08050 | 4/1994 |
| WO | 95/07364 | 3/1995 |
| WO | 01/09159 | 2/2001 |

OTHER PUBLICATIONS

Guo et al, Aptamer-Based Strategies for Stem Cell Research, 2007, Mini-Reviews in Medicinal Chemistry, 7, 701-705.*
Jellinek et al, Potent 2'-Amino-2'-deoxypyrimidine RNA Inhibitors of Basic Fibroblast Growth Factor, 1995, Biochemistry, 34: 11363-11372.*
Anthony D Keefe and Sharon T Cload, "SELEX with modified nucleotides", Current Opinion in Chemical Biology, 12(4), pp. 448-456, Aug. 2008.

* cited by examiner

*Primary Examiner* — Tracy Vivlemore
*Assistant Examiner* — Kate Poliakova-Georgantas
(74) *Attorney, Agent, or Firm* — Wenderoth, Lind & Ponack, L.L.P.

(57) ABSTRACT

Provided are an aptamer having an inhibitory activity on FGF2; a complex containing an aptamer having a binding activity or an inhibitory activity on FGF2, and a functional substance (e.g., affinity substance, labeling substance, enzyme, drug delivery vehicle, or drug and the like); a medicament, diagnostic reagent or label containing an aptamer having a binding activity or an inhibitory activity on FGF2, or a complex containing said aptamer and a functional substance; and the like.

8 Claims, 7 Drawing Sheets

Apt7          Apt8

Apt10    Apt11    Apt12    Apt13

Apt36

Apt43

Apt44

Apt45

Apt46

APTAMER TO FGF2 AND USE THEREOF

TECHNICAL FIELD

The present invention relates to an aptamer for FGF2, a method of utilizing the same, and the like.

BACKGROUND ART

Basic fibroblast growth factor (FGF2 or bFGF) is a growth to factor secreted from various cells, which is deeply involved in the cell proliferation and differentiation in developmental stages and shows high expression during tissue repair and in cancer tissues in adults.

While human FGF2 has plural isoforms, only an isoform having the least molecular weight is extracellularly secreted. This isoform is an about 18 kDa protein consisting of 154 amino acids, which is free of a sugar chain and has a basic isoelectric point of 9.4. While the function of high molecular weight isoforms (22, 22.5, 24, 34 kD) of FGF2 with different open reading frames is not clear as yet, they are considered to have a nuclear localization signal and function in the nucleus.

The human FGF family protein is known to include 22 kinds from FGF1 to FGF23 (FGF15 and FGF19 are now unified as FGF19 since they have the same molecule). By phylogenetic analysis, FGF2 is classified into FGF1 subfamily together with FGF1. The homology of amino acid sequence with FGF1 is the highest of all FGFs, and its value is 55%. FGF receptor (FGFR) is a tyrosine kinase receptor and classified into 4 subtypes. Each of FGFR1-3 is known to include b and c isoforms. FGF2 is bound by forming a dimer with FGFR1b, FGFR1c, FGFR2c and FGFR3c, and FGFR4 therefrom.

Mouse fibroblast (NIH-3T3 cell) expresses FGFR1 on the cellular membrane surface. FGFR1 is known to be activated when bound to human FGF2. When FGF2 is bound to FGFR1, MAP kinase (mitogen-activated protein kinase) pathway, PIK3 (phosphatidylinositol 3-kinase)/AKT1 (actin related gene 1) pathway and the like are activated via FRS2 (Fibroblast growth factor receptor substrate 2), Grb2 (growth factor receptor-bound protein 2), SOS, and finally, expression of various cytokine and receptor genes such as VEGF (vascular endothelial growth factor precursor)-A, VEGF-C, HGF (hepatocyte growth factor), angiopoietin-2, VEGFR, PDGFR-α (platelet-derived growth factor beta receptor-α) and the like is induced.

FGF2 has a heparin binding region and, like other FGFs, is bound to heparin and heparan sulfate. It is generally considered that FGF2 secreted from a cell is bound to a heparan sulfate of an extracellular matrix, concentrated, and protected from protease. To function as a ligand, FGF2 needs to be liberated from the extracellular matrix bound thereto, in which FGF-BP (FGF-binding protein) is reported to be involved to aid induction to FGFR.

FGF2 is known to have a strong growth, cell migration-promoting effect for vascular endothelial cells, and be deeply involved in the angiogenesis of tumor tissues. A particularly high FGF2 serum concentration in tumor with many blood vessels, for example, kidney cancer and the like, has been reported, and FGF2 is present in various other tumors such as prostate cancer, breast cancer, lung cancer and the like.

Factors such as FGF1, VEGF, TNF-α (tumor necrosis factor-α), PDGF, EGF (epidermal growth factor), MMP (matrix metallopeptidase), angiogenin and the like are involved in angiogenesis besides FGF2. These factors are secreted from tumor, angioblastic cells, supporting cells and the like, and contribute to angiogenesis as growth factors of autocrine and paracrine. However, FGF2 is different from other factors since it acts not only on vascular endothelial cells but also mesenchymal cells surrounding the endothelial cells, such as smooth muscle cell and the like. In other words, it is considered that FGF2 stimulates mesenchymal cell to promote expression of PDGF, PDGFR, VEGF, HGF and the like, and these factors enhance direct growth of vascular endothelial cells.

At present, many attempts have been made to develop a drug that inhibits abnormal angiogenesis in a tumor tissue to block a nutrient supply pathway to a tumor tissue. There is a drug actually used in clinical situations such as a humanized anti-VEGF monoclonal antibody (avastin (registered trade is mark)) developed by Genentech, which has been confirmed to show an effect for colorectal cancer and non-small cell lung cancer. However, a strong antitumor drug has not been developed yet. Many of these drugs target VEGF and PDGF, and are expected to block the initial stages of abnormal angiogenesis by targeting FGF2 that functions at more upstream.

Abnormal angiogenesis is also involved in, besides tumor, diseases such as chronic inflammations (e.g., periodontal disease, scleroderma, neovascular glaucoma, arthritis and the like), psoriasis, age-related macular degeneration and the like.

On the other hand, an attempt has been made to use the strong angiogenic action of FGF2 for the treatment of occlusive vascular disorders and wound healing. In fact, the human FGF2 preparation (fibroblast spray (registered trade mark)) of Kaken Pharmaceutical Co., Ltd. has already been approved and sold as a drug for promoting wound healing.

In recent years, applications of RNA aptamers to medicaments, diagnostic reagents, and test reagents have been drawing attention; some RNA aptamers have already been in clinical study stage or in practical use. In December 2004, the world's first RNA aptamer drug, Macugen, was approved as a therapeutic drug for age-related macular degeneration in the US. An RNA aptamer refers to an RNA that binds specifically to a target substance such as a protein, and can be prepared using the SELEX (Systematic Evolution of Ligands by Exponential Enrichment) method (see Patent documents 1-3). In the SELEX method, an RNA that binds specifically to a target substance is selected from an RNA pool with about $10^{14}$ different nucleotide sequences. The RNA structure used has a random sequence of about 40 residues, which is flanked by primer sequences. This RNA pool is allowed to be assembled with a target substance, and only the RNA that has bound to the target substance is collected using a filter and the like. The RNA collected is amplified by RT-PCR, and this is used as a template for the next round. By repeating this operation about 10 times, an RNA aptamer that binds specifically to the target substance can be acquired.

Patent document 2 describes a nucleic acid ligand (including "aptamer" in this section) of bFGF (FGF2) obtained by the SELEX method. Patent document 4 describes that a nucleic acid ligand of HGF can be used for the inhibition of tumor metastasis or angiogenesis together with a nucleic acid ligand that inhibits bFGF and, as the nucleic acid ligand that inhibits bFGF, it recites nucleic acid ligands described in patent documents 5 and 6. However, the sequences of the aptamers described in these documents are different from those of the aptamers specifically shown in the present specification. In addition, these documents do not describe or suggest the aptamers specifically shown in the present specification.

DOCUMENT LIST

Patent Documents patent document 1: WO91/19813
patent document 2: WO94/08050
patent document 3: WO95/07364
patent document 4: WO01/009159
patent document 5: U.S. Pat. No. 5,639,868
patent document 6: U.S. Pat. No. 6,759,392

SUMMARY OF THE INVENTION

Problems to be Solved by the Invention

The present invention is directed to providing an aptamer for FGF2 and a method of utilizing the same, and the like.

Means of Solving the Problems

The present inventors investigated diligently to solve the problem described above and succeeded in preparing an aptamer of good quality for FGF2, which resulted in the completion of the present invention.

Accordingly, the present invention provides the following:
[1] An aptamer that binds to FGF2.
[2] The aptamer according to [1], which inhibits binding of FGF2 and an FGF2 receptor.
[3] The aptamer according to [2], which inhibits binding of FGF2 and an FGF2 receptor but does not inhibit binding of FGF1 and a receptor.
[4] An aptamer that inhibits binding of FGF2 and an FGF2 receptor, which comprises the sequence shown by the following formula:

AGUAGUACUNGUUUAC (SEQ ID NO: 61)

wherein A is adenine, G is guanine, C is cytosine, U is uracil, and N shows a sequence consisting of 6 or 7 continuous nucleotides, each nucleotide being selected from adenine, guanine, cytosine, thymine and uracil.
[5] The aptamer according to [4], which inhibits binding of FGF2 and an FGF2 receptor, wherein the pyrimidine nucleotide is a modified nucleotide.
[6] An aptamer that inhibits binding of FGF2 and an FGF2 receptor, which comprises the sequence shown by the following formula:

GAGGGUGACGGUN'GCUGUUU (SEQ ID NO: 62)

wherein A is adenine, G is guanine, C is cytosine, U is uracil, and N' shows a sequence consisting of 7 or 10 continuous nucleotides, each nucleotide being selected from adenine, guanine, cytosine, thymine and uracil.
[7] The aptamer according to [6], which inhibits binding of FGF2 and an FGF2 receptor, wherein the pyrimidine nucleotide is a modified nucleotide.
[8] An aptamer that inhibits binding of FGF2 and an FGF2 receptor, which comprises the sequence shown by the following formula

UAGGGCN''CAGU (SEQ ID NO: 63)

wherein A is adenine, G is guanine, C is cytosine, U is uracil, and N'' shows a sequence consisting of 10-18 continuous nucleotides, each nucleotide being selected from adenine, guanine, cytosine, thymine and uracil.
[9] The aptamer according to [8], which inhibits binding of FGF2 and an FGF2 receptor, wherein the pyrimidine nucleotide is a modified nucleotide.
[10] An aptamer comprising the sequence shown by SEQ ID NO: 42, which inhibits binding of FGF2 and an FGF2 receptor.
[11] The aptamer according to [10], which inhibits binding of FGF2 and an FGF2 receptor, wherein the pyrimidine nucleotide is a modified nucleotide.
[12] An aptamer comprising the sequence shown by SEQ ID NO: 36 or 38, which inhibits binding of FGF2 and an FGF2 receptor.
[13] The aptamer according to [12], which inhibits binding of FGF2 and an FGF2 receptor, wherein the pyrimidine nucleotide is a modified nucleotide.
[14] The aptamer according to [1], which is (a) or (b) below:
(a) an aptamer comprising a nucleotide sequence selected from among SEQ ID NOs: 1-38 and 42-57 (wherein uracil may be thymine), wherein, in the nucleotide contained in the aptamer,
  (i) the 2'-position of ribose of each pyrimidine nucleotide is the same or different and is a fluorine atom, or substituted by an atom or group selected from the group consisting of a hydrogen atom, a hydroxy group and a methoxy group,
  (ii) the 2'-position of ribose of each purine nucleotide is the same or different, and is a hydroxy group, or substituted by an atom or group selected from the group consisting of a hydrogen atom, a methoxy group and a fluorine atom;
(b) an aptamer comprising a nucleotide sequence selected from among SEQ ID NOs: 1-38 and 42-57 (wherein uracil may be thymine), wherein 1 or several nucleotides are substituted, deleted, inserted or added, wherein, in the nucleotide contained in the aptamer,
  (i) the 2'-position of ribose of each pyrimidine nucleotide is the same or different and is a fluorine atom, or substituted by an atom or group selected from the group consisting of a hydrogen atom, a hydroxy group and a methoxy group,
  (ii) the 2'-position of ribose of each purine nucleotide is the same or different and is a hydroxy group, or substituted by an atom or group selected from the group consisting of a hydrogen atom, a methoxy group and a fluorine atom.
[15] The aptamer according to any one of [1] to [14], wherein the nucleotide is modified.
[16] A complex comprising the aptamer of any one of [1] to [15] and a functional substance.
[17] The complex according to [16], wherein the functional substance is an affinity substance, a labeling substance, an enzyme, a drug delivery vehicle or a drug.
[18] A medicament comprising the aptamer of any one of [1] to [15] or the complex of [16] or [17].
[19] A medicament for the treatment or prophylaxis of cancer, an autoimmune disease, an allergic disease, an inflammatory disease, or heart dysplasia, angiodysplasia or skeletal dysplasia, which comprises the aptamer of any one of [1] to [15] or the complex of [16] or [17].
[20] A diagnostic reagent comprising the aptamer of any one of [1] to [15] or the complex of [16] or [17].
[21] A detection method of FGF2, which uses the aptamer of any one of [1] to [15] or the complex of [16] or [17].

Effect of the Invention

The aptamer and the complex of the present invention can be useful as therapeutic or prophylactic drugs, diagnostic reagents or reagents for diseases such as cancer, chronic inflammation (e.g., periodontal disease, scleroderma, neovascular glaucoma, arthritis and the like), psoriasis, age-related macular degeneration and the like. The aptamer and the complex of the present invention can also be useful for the purification and concentration of FGF2, labeling of FGF2 as well as detection and quantification of FGF2.

DESCRIPTION OF EMBODIMENTS

Figure 1:
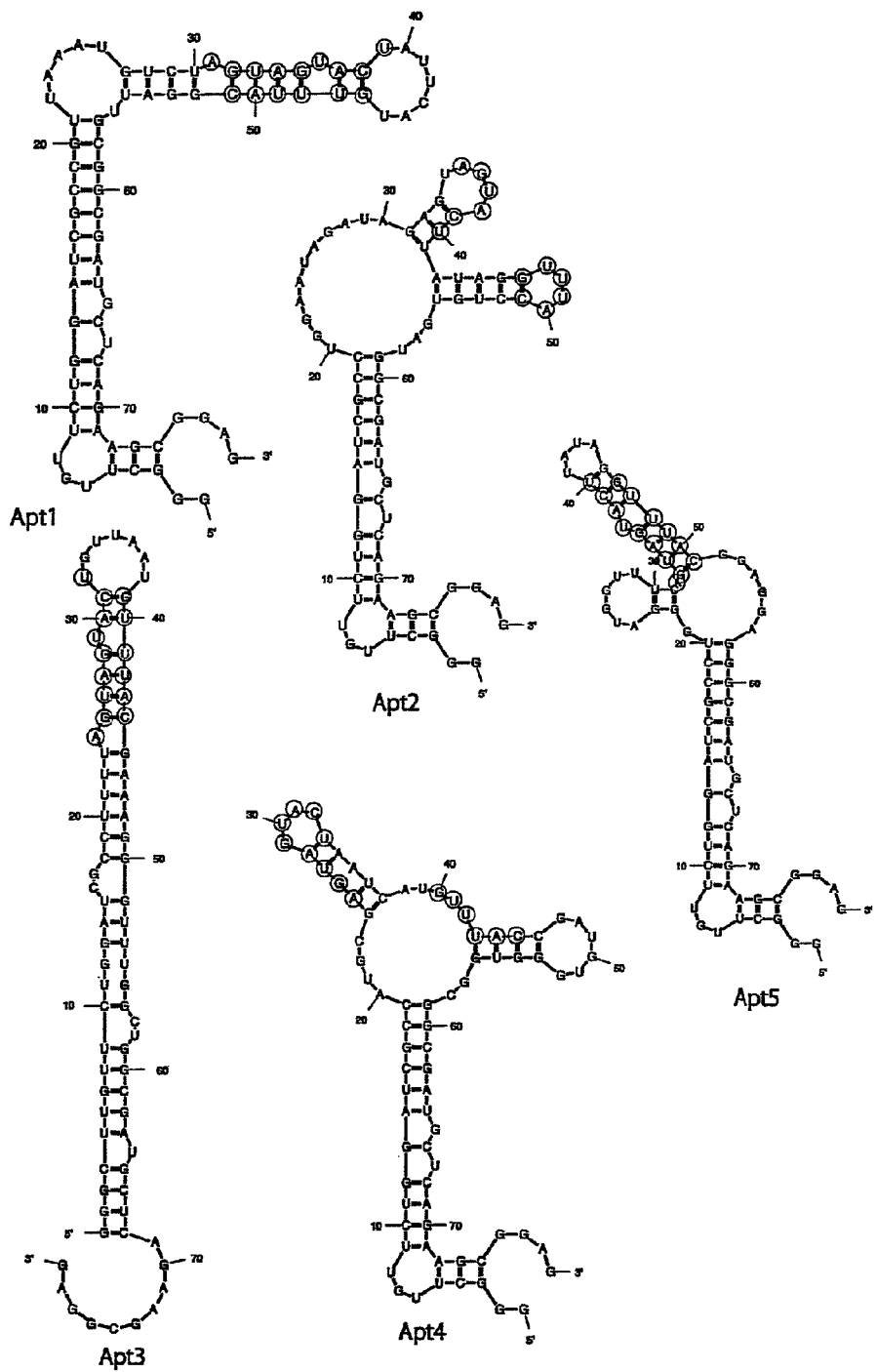
FIG. 1 respectively shows the secondary structures of aptamers shown by SEQ ID NOs: 1-5 predicted by the MFOLD program, wherein the part enclosed in a black circle shows a consensus sequence.

An aptamer refers to a nucleic acid molecule having a binding activity for a particular target molecule. The aptamer can inhibit the activity of a particular target molecule by binding to the particular target molecule. The aptamer of the present invention may be an RNA, a DNA, a modified nucleic acid or a mixture thereof. The aptamer of the present invention can also be in a linear or circular form.

The present invention provides an aptamer having a binding activity to FGF2. The aptamer of the present invention can inhibit the activity of FGF2. That is, the aptamer of the present invention has an inhibitory activity on FGF2.

The inhibitory activity on FGF2 means an inhibitory capacity on any activity FGF2 has. For example, FGF2 acts on an FGF receptor expression cell to activate signal transduction and induce production of various cell growth factors and receptors thereof. Therefore, inhibitory activity on FGF2 can be an activity to inhibit intracellular signal m transduction via an FGF receptor. Since expression of various such cell growth factors and receptors thereof results in the promotion of cell growth activity and cell Migration activity, the inhibitory activity on FGF2 means inhibition of those activities.

FGF2 is a protein that strongly expresses in the early development and differentiation, growth, regeneration and, for example, a protein having an amino acid sequence represented by Accession code EAX05222 or NP001997. FGF2 is sometimes also referred to as bFGF (basic FGF), FGFB or HBGF-2. In the present invention, FGF2 is produced in the body of an animal, or can also be produced from cultured cells such as mammalian cells of mouse and the like, insect cells, *Escherichia coli* and the like, or further can also be produced by chemical synthesis. When it is produced from cultured cells or by chemical synthesis, a variant can be easily produced by a method known per se. The "variant" of FGF2 means a protein or peptide having at least one activity from among the activities FGF2 inherently has, which has an amino acid sequence resulting from substitution, deletion, addition and the like of one to several amino acids of the known amino acid sequence of FGF2, or an amino acid sequence consisting of a part of the known amino acid sequence of FGF2. When an amino acid is substituted or added, said amino acid may be a natural amino acid or a non-natural amino acid. FGF2 in the present invention includes variants thereof.

The "FGF2 receptor" means a cell surface protein to which FGF2 binds. As the FGF2 receptor, FGFR1b, FGFR1c, FGFR2c, FGFR3c and FGFR4 are known. The FGF2 receptor referred to in the present invention may be a protein containing a natural amino acid sequence or a variant thereof. Here, the "variant" of the FGF2 receptor means a protein or peptide wherein one to several amino acids of an amino acid sequence have been substituted, deleted, added and the like, or having an amino acid sequence consisting of a part of the known amino acid sequence of FGF2, which has a binding activity to FGF2. The present invention provides an aptamer that inhibits binding of FGF2 and an FGF2 receptor.

The aptamer of the present invention can exhibit inhibitory activity against FGF2 derived from any mammals. Such mammals include primates (e.g., human, monkey), rodents (e.g., mouse, rat and guinea pig), and companion animals, domestic animals and working animals (e.g., dog, cat, horse, bovine, goat, sheep, swine).

While there is no particular limitation on the aptamer of the present invention, as far as it is capable of binding to any portions of FGF2 to inhibit the activity thereof, it is preferably an aptamer that inhibits binding of FGF2 and an FGF2 receptor, which comprises the consensus sequence shown by the following formula:

AGUAGUACUNGUUUAC (SEQ ID NO: 61)

wherein A is adenine, G is guanine, C is cytosine, U is uracil, and N shows a sequence consisting of 6 or 7 continuous nucleotides, each nucleotide being selected from adenine, guanine, cytosine, thymine and uracil (hereinafter sometimes to be indicated as "consensus sequence 1"). This sequence is a consensus sequence of the nucleotide sequences shown by the below-mentioned SEQ ID NOs: 1, 2, 3, 4 and 5, and has the same secondary structure predicted by the MFOLD program (see FIG. 1).

Figure 2:
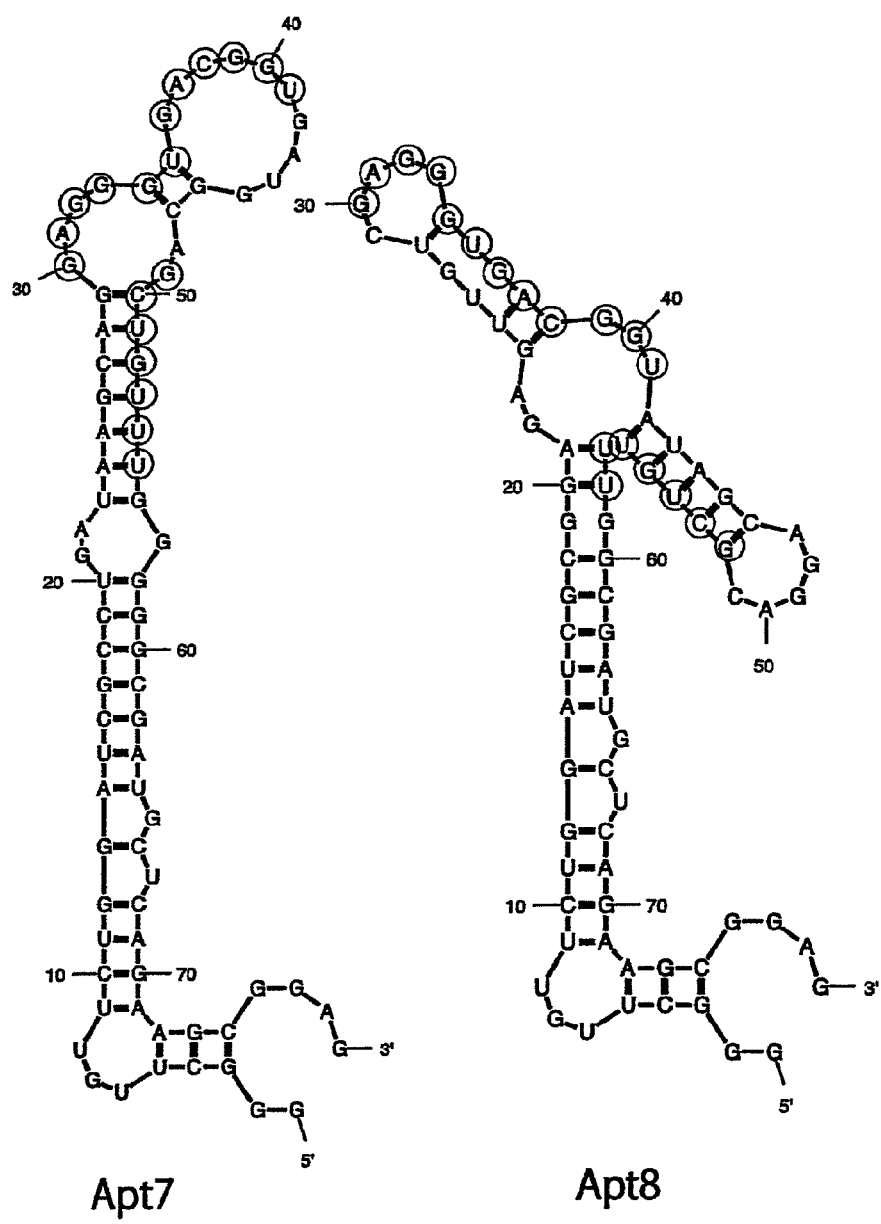
FIG. 2 shows the respective secondary structures of aptamers shown by SEQ ID NOs: 7 and 8 predicted by the MFOLD program, wherein the part enclosed in a black circle shows a consensus sequence.

While there is no particular limitation on the aptamer of the present invention, as far as it is capable of binding to any portions of FGF2 to inhibit the activity thereof, it is preferably an aptamer that inhibits binding of FGF2 and an FGF2 recep tor, and comprises the consensus sequence shown by the following formula:

GAGGGUGACGGUN'GCUGUUU (SEQ ID NO: 62)

wherein A is adenine, G is guanine, C is cytosine, U is uracil, and N' shows a sequence consisting of 7 or 10 continuous nucleotides, each nucleotide being selected from adenine, guanine, cytosine, thymine and uracil (hereinafter sometimes to be indicated as "consensus sequence 2"). This sequence is a consensus sequence of the nucleotide sequences shown by the below-mentioned SEQ ID NOs: 7 and 8, and has the same secondary structure predicted by the MFOLD program (see FIG. 2).

Figure 3:
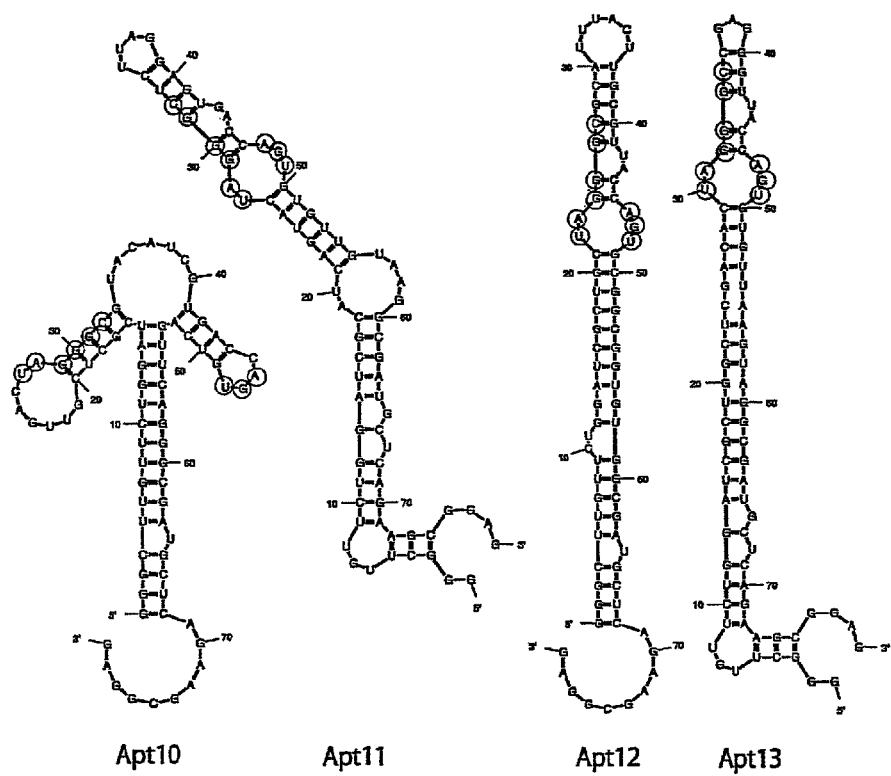
FIG. 3 shows the respective secondary structures of aptamers shown by SEQ ID NOs: 10-13 predicted by the MFOLD program, wherein the part enclosed in a black circle shows a consensus sequence.

While there is no particular limitation on the aptamer of the present invention, as far as it is capable of binding to any portions of FGF2 to inhibit the activity thereof, it is preferably an aptamer that inhibits binding of FGF2 and an FGF2 receptor, and comprises the consensus sequence shown by the following formula:

UAGGGCN''CAGU (SEQ ID NO: 63)

wherein A is adenine, G is guanine, C is cytosine, U is uracil, and N'' shows a sequence consisting of 10-18 continuous nucleotides, each nucleotide being selected from adenine, guanine, cytosine, thymine and uracil (hereinafter sometimes to be indicated as "consensus sequence 3"). This sequence is a consensus sequence of the nucleotide sequences shown by the below-mentioned SEQ ID NOs: 10, 11, 12 and 13, and has the same secondary structure predicted by the MFOLD program (see FIG. 3).

Figure 7:
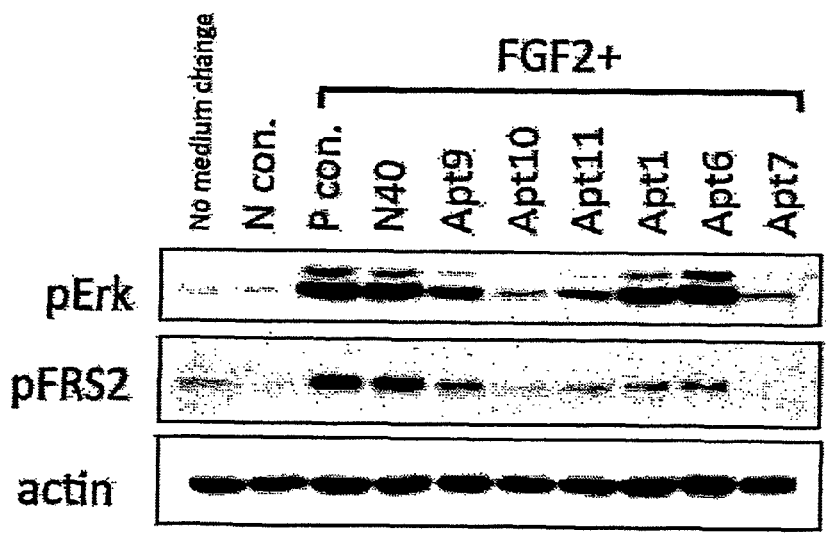
FIG. 7 shows the results of Western blotting showing that the aptamers shown by SEQ ID NOs: 1, 6, 7, 9-11 inhibit the physiological activity of human FGF2.

While there is no particular limitation on the aptamer of the present invention, as far as it is capable of binding to any portions of FGF2 to inhibit the activity thereof, it is preferably an aptamer that inhibits binding of FGF2 and an FGF2 receptor, and comprises the sequence of gggc(F)u(F)u(F)gu(F)u(F)c(F)u(F)ggau(F)c(F)gc(F)u(F) c(F)u(F)ggau(F)c(F)gc(F)u(F)gau(F)aagc (F)aggagggu(F) gac(F)ggu(F)gau(F)ggc(F)agc(F)u(F)gu(F)u(F)u(F)g ggggc (F)gau(F)gc(F)u(F)c(F)agaagc(F)ggag (SEQ ID NO: 7) (see FIG. 7).

While there is no particular limitation on the aptamer of the present invention, as far as it is capable of binding to any portions of FGF2 to inhibit the activity thereof, it is preferably an aptamer that inhibits binding of FGF2 and an FGF2 receptor, and comprises the sequence of
gggc(F)u(F)u(F)gu(F)u(F)c(F)u(F)ggau(F)c(F)gc(F)gau(F)
  gc(F)aag u(F)u(F)ac(F)c(F)agu(F)gu(F)agc(F)u(F)agu(F)
  u(F)ac(F)u(F)agggc (F)gu(F)gu(F)gu(F)u(F)ggc(F)gau
  (F)gc(F)u(F)c(F)agaagc(F)ggag (SEQ ID NO: 9);
gggc(F)u(F)u(F)gu(F)u(F)c(F)u(F)ggau(F)c(F)gc(F)u(F)c
  (F)gu(F)u (F)gac(F)u(F)agggc(F)gu(F)ac(F)au(F)c(F)gu
  (F)gac(F)c(F)agu(F)g u(F)c(F)agu(F)u(F)c(F)agggc(F)
  gau(F)gc(F)u(F)c(F)agaagc(F)ggag (SEQ ID NO: 10); or
gggc(F)u(F)u(F)gu(F)u(F)c(F)u(F)ggau(F)c(F)gc(F)au(F)c
  (F)agu(F) ac(F)u(F)agggc(F)u(F)c(F)u(F)u(F)aggagu(F)
  gac(F)c(F)agu(F)gu( F)gu(F)u(F)gu(F)aaggc(F)gau(F)gc
  (F)u(F)c(F)agaagc(F)ggag (SEQ ID NO: 11) (see FIG. 7).

Figure 9:
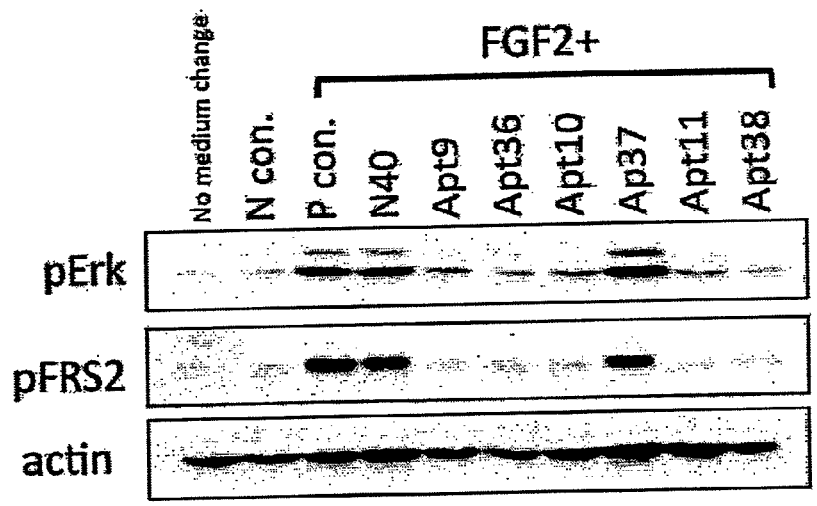
FIG. 9 shows the results of Western blotting showing that the aptamers shown by SEQ ID NO: 36 and 38 inhibit the physiological activity of human FGF2.

While there is no particular limitation on the aptamer of the present invention, as far as it is capable of binding to any portions of FGF2 to inhibit the activity thereof, it is preferably an aptamer that inhibits binding of FGF2 and an FGF2 receptor, and comprises the sequence of
ggggc(F)aagu(F)u(F)ac(F)c(F)agu(F)gu(F)agc(F)u(F)agu
  (F)u(F)ac(F)u (F)agggc(F)gu(F)gu(F)c(F)c(F)c(F) (SEQ
  ID NO: 36) (see FIG. 9).

While there is no particular limitation on the aptamer of the present invention, as far as it is capable of binding to any portions of FGF2 to inhibit the activity thereof, it is preferably an aptamer that inhibits binding of FGF2 and an FGF2 receptor, shows FGF2 signaling inhibitory activity on the cell, and comprises the sequence of
gggu(F)ac(F)u(F)agggc(F)u(F)c(F)u(F)u(F)aggagu(F)gac
  (F)c(F)agu (F)gu(F)gc(F)c(F)c(F) (SEQ ID NO: 38) (see
  FIG. 9).

Figure 10:
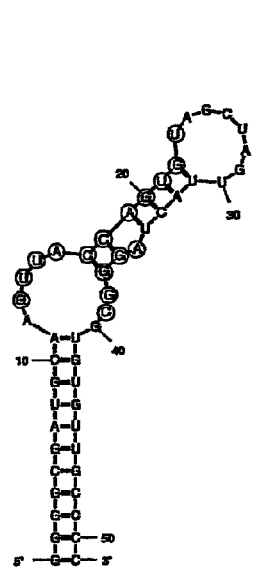
FIG. 10 shows the secondary structures of aptamers shown by SEQ ID NOs: 36 and 43-46 predicted by the MFOLD program, wherein the part enclosed in a black circle shows a consensus sequence.
Figure 10:
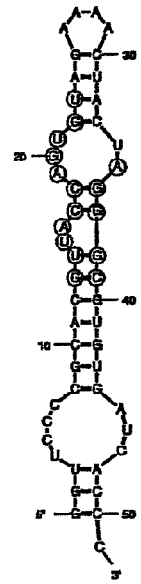
Figure 10:
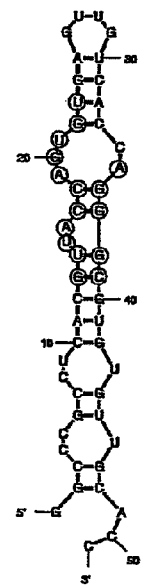
Figure 10:
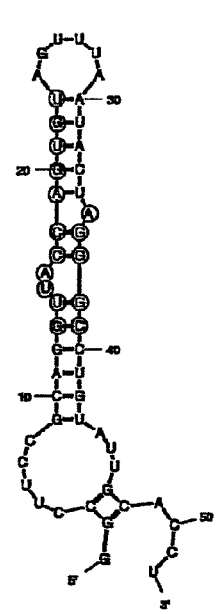
Figure 10:
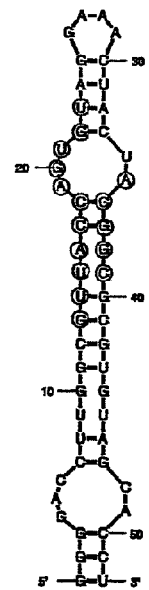

While there is no particular limitation on the aptamer of the present invention, as far as it is capable of binding to any portions of FGF2 to inhibit the activity thereof, it is preferably an aptamer that inhibits binding of FGF2 and an FGF2 receptor, shows FGF2 signaling inhibitory activity on the cell, and comprises the sequence of
gu(F)u(F)ac(F)c(F)agu(F)gu(F)nnnnnnnnnnnagggc(F)
  (SEQ ID NO: 42). This sequence is a consensus sequence
  of the nucleotide sequences shown by the below-mentioned SEQ ID NOs: 43-46 (hereinafter sometimes to be
  indicated as "consensus sequence 4"), and has the same
  secondary structure predicted by the MFOLD program
  (see FIG. 10).

These sequences are different from the sequences of the nucleic acid ligands described in the aforementioned patent document 2, patent document 5 and patent document 6.

The length of the aptamer of the present invention is not particularly limited, and can usually be about 10 to about 200 nucleotides, and can be, for example, not more than about 100 nucleotides, preferably not more than about 50 nucleotides, more preferably not more than about 40 nucleotides, most preferably not more than about 35 nucleotides. When the total number of nucleotides is smaller, chemical synthesis and mass-production will be easier, and there is a major advantage in terms of cost. It is also thought that chemical modification is easy, stability in the body is high, and toxicity is low.

Each nucleotide contained in the aptamer of the present invention is the same or different and can be a nucleotide comprising a hydroxyl group at the 2' position of ribose (e.g., ribose of pyrimidine nucleotide, ribose of purine nucleotide) (i.e., a non-substituted nucleotide) or a nucleotide wherein hydroxyl group is substituted (modified) by any atom or group at the 2' position of ribose (sometimes to be indicated as "substituted nucleotide" or "modified nucleotide" in the present invention).

As examples of any such atom or group, a nucleotide substituted by a hydrogen atom, a fluorine atom or an —O-alkyl group (e.g., —O-Me group), an —O-acyl group (e.g., —O—CHO group), or an amino group (e.g., —NH$_2$ group) can be mentioned. The aptamer of the present invention can also be the modified nucleotide wherein at least one kind (e.g., 1, 2, 3 or 4 kinds) of nucleotide comprises a hydroxyl group, or the above-described any atom or group, for example, at least two kinds (e.g., 2, 3 or 4 kinds) of groups selected from the group consisting of a hydrogen atom, a fluorine atom, a hydroxyl group and a —O-Me group, at the 2' position of ribose.

In the aptamer of the present invention, all pyrimidine nucleotides are the same or different and each can be a nucleotide substituted by a fluorine atom, or a nucleotide substituted by any atom or group mentioned above, preferably an atom or group selected from the group consisting of a hydrogen atom, a hydroxyl group and a methoxy group at the 2' position of ribose.

In the aptamers of the present invention, moreover, all purine nucleotides are the same or different and each can be a nucleotide substituted by a hydroxyl group or a nucleotide substituted by any atom or group mentioned above, preferably an atom or a group selected from the group consisting of a hydrogen atom, a methoxy group, and a fluorine atom, at the 2'-position of ribose.

The aptamer of the present invention can also be one wherein all nucleotides are substituted by a hydroxyl group, or any atom or group mentioned above, for example, the identical atom or group selected from the group consisting of a hydrogen atom, a fluorine atom, a hydroxyl group and a —O-Me group, at the 2' position of ribose.

The aptamer of the present invention can be characterized in that it can inhibit the activity of FGF2 but cannot inhibit the activity of FGF1. In addition, the aptamer of the present invention can be characterized in that it can inhibit binding of FGF2 and an FGF2 receptor but cannot inhibit binding of FGF1 and an FGF1 receptor. FGF1 is an FGF family protein, and is most similar to FGF2.

The aptamer of the present invention can also be:
(a) an aptamer comprising a nucleotide sequence selected from among consensus sequences 1-4 (wherein uracil may be thymine);
(b) an aptamer comprising a nucleotide sequence selected from among consensus sequences 1-4 (wherein uracil may be thymine), wherein one to several nucleotides are substituted, deleted, inserted or added; and
(c) a conjugate selected from the group consisting of a conjugate of a plurality of aptamers (a) above, a conjugate of a plurality of aptamers (b) above, and a conjugate of a plurality of aptamers (a) and (b) above.

In (b) above, the number of nucleotides substituted, deleted, inserted or added is not particularly limited as long as the aptamer still binds to FGF2 even after the substitution, deletion, insertion or addition. It can be, for example, not more than about 30, preferably not more than about 20, more preferably not more than about 10, still more preferably not more than 5, most preferably 4, 3, 2 or 1. In (c) above, conjugation can be achieved by tandem binding. In the conjugation, a linker may be utilized. As the linker, nucleotide chains (e.g., 1 to about 20 nucleotides) and non-nucleotide chains (e.g., —(CH$_2$)$_n$-linker, —(CH$_2$CH$_2$O)$_n$-linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described conjugate of a plurality thereof is not particularly limited, as long as it is two or more, and the plurality can be, for example, 2, 3 or 4.

Each of the nucleotides in (a) to (c) above, whether the same or different, can be a nucleotide comprising a hydroxyl group at the 2' position of ribose (e.g., ribose of pyrimidine nucleotide), or a nucleotide wherein a hydroxyl group is substituted by any atom or group (e.g., a hydrogen atom, fluorine atom or —O-Me group) at the 2' position of ribose.

For example, it may be an aptamer wherein, in each nucleotide contained in the above-mentioned (a)-(c),
(i) all pyrimidine nucleotides are the same or different and each is a nucleotide substituted by a fluorine atom, or a nucleotide substituted by an atom or group mentioned above, preferably an atom or group selected from the group consisting of a hydrogen atom, a hydroxyl group and a methoxy group at the 2' position of ribose; and
(ii) all purine nucleotides are the same or different and each is a nucleotide substituted by a hydroxyl group, or a nucleotide substituted by an atom or group mentioned above, preferably an atom or a group selected from the group consisting of a hydrogen atom, a methoxy group, and a fluorine atom at the 2'-position of ribose. The present invention also provides the above-mentioned aptamer.

The aptamer of the present invention can also be:
(a') an aptamer comprising a nucleotide sequence selected from among SEQ ID NOs:1-38 and 42-57 (wherein uracil may be thymine);
(b') an aptamer comprising a nucleotide sequence selected from among SEQ ID NOs:1-38 and 42-57 (wherein uracil may be thymine), wherein one to several nucleotides are substituted, deleted, inserted or added;
(c') a conjugate selected from the group consisting of a conjugate of a plurality of aptamers (a') above, a conjugate of a plurality of aptamers (b') above, and a conjugate of a plurality of aptamers (a') and (b') above.

Of the above-mentioned (a')-(c'), preferred are (a')-(c') wherein the nucleotide sequence selected from any of SEQ ID NOs: 1-38 and 42-57 is the sequence of SEQ ID NO: 36 or 38.

In (b') above, the number of nucleotides substituted, deleted, inserted or added is not particularly limited as long as the aptamer still binds to FGF2 even after the substitution, deletion, insertion or addition. It can be, for example, not more than about 30, preferably not more than about 20, more preferably not more than about 10, still more preferably not more than 5, most preferably 4, 3, 2 or 1. In (c') above, conjugation can be achieved by tandem binding. In the conjugation, a linker may be utilized. As the linker, nucleotide chains (e.g., 1 to about 20 nucleotides) and non-nucleotide chains (e.g., —(CH$_2$)$_n$-linker, —(CH$_2$CH$_2$O)$_n$-linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described a conjugate of a plurality thereof is not particularly limited, as long as it is two or more, and the plurality can be, for example, 2, 3 or 4.

Each of the nucleotides in (a') to (c') above, whether the same or different, can be a nucleotide comprising a hydroxyl group at the 2' position of ribose (e.g., ribose of pyrimidine nucleotide), or a nucleotide wherein a hydroxyl group is substituted by any atom or group (e.g., a hydrogen atom, fluorine atom or —O-Me group) at the 2' position of ribose.

For example, it may be an aptamer wherein, in each nucleotide contained in the above-mentioned (a')-(c'),
(i) all pyrimidine nucleotides are the same or different and each can be a nucleotide substituted by a fluorine atom, or a nucleotide substituted by any atom or group mentioned above, preferably an atom or group selected from the group consisting of a hydrogen atom, a hydroxyl group and a methoxy group at the 2' position of ribose; and
(ii) all purine nucleotides are the same or different and each can be a nucleotide substituted by a hydroxyl group, or a nucleotide substituted by any atom or group mentioned above, preferably an atom or a group selected from the group consisting of a hydrogen atom, a methoxy group, and a fluorine atom at the 2'-position of ribose. The present invention also provides the above-mentioned aptamer.

The aptamer of the present invention may be one wherein a sugar residue (e.g., ribose) of each nucleotide has been modified to increase the FGF2 binding activity, stability, drug deliverability and the like. As examples of the modification in a sugar residue, replacement of oxygen atom at the 2'-position, 3'-position and/or 4'-position of the sugar residue with another atom, and the like can be mentioned. As the kind of the modification, fluorination, O-alkylation (e.g., O-methylation, O-ethylation), O-arylation, S-alkylation (e.g., S-methylation, S-ethylation), S-arylation, and amination (e.g., —NH$_2$) can be mentioned. Such alterations in the sugar residue can be performed by a method known per se (see, for example, Sproat et al., (1991) Nucl. Acid. Res. 19, 733-738;

Cotton et al., (1991) Nucl. Acid. Res. 19, 2629-2635; Hobbs et al., (1973) Biochemistry 12, 5138-5145).

The aptamer of the present invention may also have a nucleic acid base (e.g., purine or pyrimidine) altered (e.g., chemical substitution) to increase the FGF2 binding activity and the like. As examples of such alterations, pyrimidine alteration at 5-position, purine alteration at 6- and/or 8-position(s), alteration with an extracyclic amine, substitution with 4-thiouridine, and substitution with 5-bromo or 5-iodo-uracil can be mentioned. The phosphate group contained in the aptamer of the present invention may be altered to confer resistance to nuclease and hydrolysis. For example, the P(O)O group may be replaced with P(O)S (thioate), P(S)S (dithioate), P(O)NR$_2$ (amidate), P(O)R, R(O)OR', CO or CH$_2$ (formacetal) or 3'-amine (—NH—CH$_2$—CH$_2$—) [wherein each unit of R or R' is independently H or a substituted or unsubstituted alkyl (e.g., methyl, ethyl)].

The linking group is, for example, —O—, —N— or —S—, and nucleotides can bind to an adjoining nucleotide via these linking groups.

The alterations may also include alterations such as capping at 3' and 5'.

An alteration can further be performed by adding to an end a polyethyleneglycol, amino acid, peptide, inverted dT, nucleic acid, nucleosides, Myristoyl, Lithocolic-oleyl, Docosanyl, Lauroyl, Stearoyl, Palmitoyl, Oleoyl, Linoleoyl, other lipids, steroids, cholesterol, caffeine, vitamins, pigments, fluorescent substances, anticancer agent, toxin, enzymes, radioactive substance, biotin and the like. For such alterations, see, for example, U.S. Pat. Nos. 5,660,985 and 5,756,703.

The aptamer of the present invention can be chemically synthesized as disclosed herein and by a method known per se in the art. An aptamer binds to the target substance in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target substance can be substituted. In particular, because the region of stem structure has already formed base pairs and faces the inside of the double helical structure, nucleic acid bases are unlikely to bind directly to the target substance. Therefore, even when a base pair is substituted with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change substantially.

An aptamer can be prepared by utilizing the SELEX method or an improved version thereof (e.g., Ellington et al., (1990) Nature, 346, 818-822; Tuerk et al., (1990) Science, 249, 505-510). In the SELEX method, by increasing the number of rounds or using a competing substance, an aptamer exhibiting a stronger binding potential for the target substance is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target substance, but this does not mean binding to an active site of the target substance. Therefore, the aptamers obtained by SELEX do not necessarily act on the function of the target substance. FGF2 is a basic protein, and is thought to be likely to allow nucleic acids to bind thereto nonspecifically. An aptamer that does not bind to an active site does not influence the activity of the target substance. In fact, the RNA used for control did not inhibit the binding of FGF2 and an FGF2 receptor.

Using the active aptamer thus selected, optimized SELEX can be performed to obtain an aptamer possessing higher activity. In the optimized SELEX, SELEX is performed again after preparing a template wherein an aptamer with a determined sequence is partially randomized or a template doped with about 10 to 30% of random sequences.

An aptamer obtained by SELEX has a length of about 80 nucleotides, and this is difficult to prepare as a pharmaceutical as it is. Hence, it is necessary to repeat try-and-error efforts to shorten the aptamer to a length of about 50 nucleotides or less enabling easy chemical synthesis. Depending on the primer design for an aptamer obtained by SELEX, the ease of the subsequent minimization operation changes. Unless the primer is designed successfully, subsequent development will be impossible even if an aptamer with activity is selected by SELEX. In the present invention, an aptamer retaining activity even with 41 nucleotides (SEQ ID NO: 36) and 35 nucleotides (SEQ ID NO: 38) can be obtained, and these sequences were found to be particularly important for binding with FGF2.

Aptamers are altered easily since they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

When a region important to the binding of the obtained aptamer with the target substance is identified by repeated try-and-error efforts as described above, the activity remains unchanged in many cases even when a new sequence is added to both ends of the sequence. The length of the new sequence is not particularly limited.

As mentioned earlier, modifications, like sequences, permit a wide range of design or alterations.

As stated above, aptamers permit a wide range of design or alterations. The present invention also provides a production method of aptamer that enables a wide range of design or alteration of an aptamer comprising a specified sequence (e.g., a sequence corresponding to a portion selected from among stem regions, internal loop regions, hairpin loop regions and single-strand regions: hereinafter, abbreviated as fixed sequence as required).

For example, the production method of such aptamer includes production of an aptamer comprising a fixed sequence by using a single kind of nucleic acid molecule consisting of a nucleotide sequence shown by:

| Primer sequence (i) |—(N)a-fixed sequence (N)b—| Primer sequence (ii) |

[wherein (N)a represents a nucleotide chain consisting of "a" units of N; (N)b represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be any numbers, and can be, for example, 1 to about 100, preferably 1 to about 50, more preferably 1 to about 30, still more preferably 1 to about 20 or 1 to about 10], or plural kinds of nucleic acid molecules (e.g., library of nucleic acid molecule different in the number of a, b etc.) and primer pairs corresponding to the primer sequences (i) and (ii), respectively.

The present invention also provides a complex comprising the aptamer of the present invention and a functional substance bound thereto. The bond between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; reast agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and Vero toxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction endonuclease.

The aptamer or the complex of the present invention can be used as, for example, a pharmaceutical or a diagnostic reagent, a test reagent or a reagents. Particularly, it is useful as a therapeutic or prophylactic medicament, or a diagnostic reagent, a test reagent or a reagent for the diseases such as cancer, autoimmune diseases, allergic disease, inflammatory disease, or heart dysplasia, angiodysplasia, skeletal dysplasia.

Examples of the target disease of the above-mentioned medicament include esophagus cancer, thyroid cancer, urinary bladder cancer, colorectal cancer, gastric cancer, pancreatic cancer, thoracic cancer, liver cancer, lung cancer, non-small cell lung cancer, breast cancer, neuroblastoma, neuroglastoma, glioblastoma, uterine cancer, cervical cancer, ovarian cancer, Wilms' tumor, prostate cancer, periodontal disease, multiple sclerosis, systemic lupus erythematosus (SLE), scleroderma, Sjogren's syndrome, polymyositis (PM), dermatomyositis (DM), rheumatoid arthritis (RA), osteoarthritis (OA), inflammatory enteritis (Crohn's disease and the like), progressive systemic sclerosis (PSS), periarteritis nodosa (PN), thyroid gland disease (Graves' disease and the like), Guillain-Barre syndrome, primary biliary cirrhosis (PBC), idiopathic thrombocytopenic purpura, autoimmune hemolytic anemia, myasthenia gravis (MG), amyotrophic lateral sclerosis (ALS), Type I diabetes mellitus, psoriasis, asthma, neutrophil dysfunction, eosinophilic pneumonia, idiopathic lung fibrosis, hypersensitive pneumonia, transplant rejection, graft-versus-host disease, asthma, allergic rhinitis, atopic dermatitis, food hypersensitivity, urticaria, postoperative adhesion, endometriosis, adult periodontitis, bronchitis, COPD, infections, bone and articular diseases such as craniosynostosis, achondroplasia, hypochondroplasia and the like, hypophosphatemic rickets.osteohalisteresis and the like.

In addition, the aptamer or complex of the present invention can also be used as a drug delivery agent, probe for in vivo imaging, probe for measuring blood concentration of FGF2, probe for tissue staining, probe for ELISA, ligand for FGF2 separation and purification.

FGF2 is known to act on various cells such as fibroblast, stem cell, endothelial cell, epithelial cell, chondrocyte, osteoblast, neural progenitor cell, bone marrow-derived interstitial cell, T cell, macrophage, neutrophil, hematopoietic cell, tumor cell and the like. FGF2 acts on these cells via a receptor to activate MAPK cascade, PLCy cascade, PI3 kinase cascade and the like in the downstream, and further control expression of the gene in the downstream. Therefore, the aptamer or complex of the present invention can be used as a therapeutic or prophylactic medicament, or a diagnostic reagent, a test reagent or a reagent for the diseases related to these cells and signal transduction pathway and the like.

The medicament of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not imitative.

Preparations suitable for oral administration are a solution prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The medicament of the present invention can be coated by a method known per se for the purpose of taste masking, enteric dissolution, sustained release and the like as necessary. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), pigments (e.g., ferric oxide red, titanium dioxide and the like) and the like are used. The medicament may be a rapid-release preparation or sustained-release preparation. Examples of the base of the sustained-release preparation include liposome, atelocollagen, gelatin, hydroxyapatite, PLGA and the like.

As preparations suitable for parenteral administration (e.g., intravenous administration, subcutaneous administration, intramuscular administration, topical administration, intraperitoneal administration, intranasal administration, pulmonary administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use. In addition to liquid injections, inhalants and ointments are also acceptable. In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required.

Here, as examples of the surfactant, oleic acid, lecithin, diethylene glycol dioleate, tetrahydrofurfuryl oleate, ethyl oleate, isopropyl myristate, glyceryl trioleate, glyceryl monolaurate, glyceryl monooleate, glyceryl monostearate, glyceryl monolysinoate, cetyl alcohol, stearyl alcohol, polyethyleneglycol 400, cetylpyridinium chloride, sorbitan trioleate (trade name, Span 85), sorbitan monoleate (trade name, Span 80), sorbitan monolaurate (trade name, Span 20), polyoxyethylene hardened castor oil (trade name, HCO-60), polyoxyethylene (20) sorbitan monolaurate (trade name, Tween 20), polyoxyethylene (20) sorbitan monooleate (trade name, Tween 80), lecithin of natural resource origin (trade name, Epiclon), oleylpolyoxyethylene (2) ether (trade name, Brij 92), stearyl polyoxyethylene (2) ether (trade name, Brij 72), lauryl polyoxyethylene (4) ether (trade name, Brij 30), oleylpolyoxyethylene (2) ether (trade name, Genapol 0-020), block copolymer of oxyethylene and oxypropylene (trade name, Synperonic) and the like can be mentioned. Span, Tween, Epiclon, Brij, Genapol and Synperonic are trademarks.

As examples of the oil, corn oil, olive oil, cottonseed oil, sunflower oil and the like can be mentioned. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an active ingredient, and used as a preparation.

An inhalant can be produced according to a conventional method. Specifically, an inhalant can be produced by powdering or liquefying the above-described aptamer and complex of the present invention, blending it in an inhalation propellant and/or carrier, and filling them in an appropriate inhalation vessel. When the above-described aptamer and complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as nitrogen gas and carbon dioxide gas and the like can be mentioned.

The dosage of the medicament of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The present invention also provides a solid phase carrier having the aptamer and the complex of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicone substrates, alumina substrates and the like, and substrates prepared by coating these substrates with a polymer and the like can be mentioned. As examples of the resin, agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of aryldextran and N,N'-methylenebisacrylamide, monodispersed synthetic polymers, monodispersed hydrophilic polymers, Sepharose, Toyopearl and the like can be mentioned, and also resins prepared by binding various functional groups to these resins were included. The solid phase carrier of the present invention can be useful in, for example, purifying, detecting and quantifying FGF2.

The aptamer and the complex of the present invention can be immobilized onto a solid phase carrier by a method known per se. For example, a method that introduces an affinity substance (e.g., those described above) or a predetermined functional group into the aptamer or the complex of the present invention, and then immobilizes the aptamer and complex onto a solid phase carrier via the affinity substance or predetermined functional group can be mentioned. The present invention also provides a method of immobilizing the aptamer or complex of the present invention on a solid phase carrier, and a solid phase carrier obtained thereby. The predetermined functional group can be a functional group that can be subjected to a coupling reaction; for example, an amino group, a thiol group, a hydroxyl group, and a carboxyl group can be mentioned. The present invention also provides an aptamer having such a functional group introduced thereto.

The present invention also provides a method of purifying and concentrating FGF2. In particular, the purification method of the present invention makes it possible to separate FGF2 from other FGF family proteins. The method of purification and concentration of the present invention can comprise adsorbing FGF2 to the solid phase carrier of the present invention, and eluting the adsorbed FGF2 with an eluent. Adsorption of FGF2 to the solid phase carrier of the present invention can be achieved by a method known per se. For example, a FGF2-containing sample (e.g., bacterial or cell culture or culture supernatant, blood) is introduced into the solid phase carrier of the present invention or a composition containing the same. FGF2 can be eluted using an eluent such as a neutral solution. There is no limitation on the neutral eluent, which can have a pH of, for example, about 6 to about 9, preferably about 6.5 to about 8.5, and more preferably about 7 to about 8. The neutral solution can also comprise, for example, a potassium salt (e.g., KCl), a magnesium salt (e.g., $MgCl_2$), a surfactant (e.g., Tween 20, Triton, NP40), and glycerin.

The method of purification and concentration of the present invention can further comprise washing the solid phase carrier using a washing solution after FGF2 adsorption. Examples of the washing solution include those containing urea, a chelating agent (e.g., EDTA), Tris, an acid, an alkali, Transfer RNA, DNA, surfactants such as Tween 20, salts such as NaCl and the like. The method of purification and concentration of the present invention can still further comprise heating the solid phase carrier. This step enables the regeneration and sterilization of the solid phase carrier.

The aptamer or complex of the present invention can be utilized as a detection probe, particularly, detection probe of FGF2. A labeling method of aptamer is not particularly limited, and a method known per se is applicable. Examples of such method include labeling with radioisotope, labeling with fluorescence dye or fluorescent protein, and the like.

The present invention also provides a method of detecting and quantifying FGF2. In particular, the present invention makes it possible to detect and quantify FGF2 separately from the proteins of other family proteins. The method of detection and quantitation of the present invention can comprise measuring FGF2 by utilizing the aptamer of the present invention (e.g., by the use of the complex and solid phase carrier of the present invention). The method of detecting and quantifying FGF2 can be performed in the same manner as an immunological method, except that the aptamer of the present invention is used in place of an antibody. Therefore, by using the aptamer of the present invention in place of an antibody, in the same manner as such methods as enzymeimmunoassay (EIA) (e.g., direct competitive ELISA, indirect competitive ELISA, sandwich ELISA), radioimmunoassay (RIA), fluorescent immunoassay (FIA), Western blot method (e.g., use instead of secondary antibody in Western blot method), immunohistochemical staining method, and cell sorting method, detection and quantitation can be performed. These methods can be useful in, for example, measuring FGF2 contents in living organisms or biological samples, and in diagnosing a disease associated with FGF2.

The disclosures in all publications mentioned herein, including patents and patent application specifications, are incorporated by reference herein in the present invention to the extent that all of them have been given expressly.

The present invention is hereinafter described in more detail by means of the following Examples, which, however, never limit the scope of the invention.

EXAMPLES

Example 1

Preparation of Nucleic Acids that Binds Specifically to FGF2

Nucleic acid that binds specifically to FGF2 was prepared using the SELEX method. The SELEX was performed by improving the method of Ellington et al. (Ellington and Szostak, Nature 346, 818-822, 1990) and the method of Tuerk et al. (Tuerk and Gold, Science 249, 505-510, 1990). Human FGF2 (manufactured by Peprotech Inc.) was used as a target substance. FGF2 was immobilized on agarose resin (NHS-activated Sepharose, manufactured by GE Healthcare) by amino coupling. The amino coupling was performed according to the manual of GE Healthcare. The amount of immobilization was confirmed by examining the FGF2 solution before immobilization and the supernatant immediately after immobilization by SDS-PAGE. As a result of SDS-PAGE, FGF2 band was not detected from the supernatant, which confirmed that almost all FGF2 used was coupled. About 400 pmol of FGF2 was immobilized on about 10 μL of resin.

The RNA used in the first round (40N-RNA) was obtained by transcribing a chemically synthesized DNA using the DuraScribe (trademark) T7 Transcription Kit (manufactured by Epicentre). The RNA obtained by this method has the 2'-position of the ribose of the pyrimidine nucleotide fluoro-substituted. The DNA 95 nucleotides long shown below, having a primer sequence at each end of a 40-nucleotide random sequence was used as DNA template. The DNA template and the primers were prepared by chemical synthesis. The DNA template and primers used are shown below.

```
DNA template :
                                        (SEQ ID NO: 39)
5'-taatacgactcactatagggcttgttctggatcgc-40N- ggcgatgctcagaagcggag-3' primer Fwd:
                                        (SEQ ID NO:40)
5'-taatacgactcactatagggcttgttctggatcgc-3' primer Rev:
                                        (SEQ ID NO:41)
5'-ctccgcttctgagcatcgcc-3'
```

N represents any one of A, G, C and T. The primer Fwd comprises a promoter sequence of T7 RNA polymerase. The variation of the RNA pool used in the first round was theoretically $10^{14}$.

RNA pool was added to the resin on which FGF2 was immobilized, and the mixture was maintained at room temperature for 30 min. After 30 min, the resin was washed with solution A to remove RNA not bound to FGF2. Here, solution A is a mixed solution of 145 mM sodium chloride, 5.4 mM potassium chloride, 1.8 mM calcium chloride, 0.8 mM magnesium chloride, 20 mM tris (pH 7.6), 0.05% Tween 20. The RNA bound to FGF2 was recovered by adding eluate and stirring the mixture at room temperature for 10 min. As eluate, solution A adjusted to pH 7.6 by adding 6M guanidine hydrochloride was used. The recovered RNA was amplified by RT-PCR, transcribed using DuraScribe (trademark) T7 Transcription Kit and used as a pool for the next round. With the above as 1 round, a similar operation was performed for 8 rounds. After completion of SELEX, the PCR product was cloned into a pGEM-T Easy vector (manufactured by Promega), which was used to tranform *Escherichia coli* strain DH5a (manufactured by Toyobo). The plasmid was extracted from a single colony and the base sequences of 97 clones were examined by DNA sequencer (3130×1 Genetic Analyzer, manufactured by ABI).

After 10 rounds of SELEX, the sequences were examined; sequence convergence was seen.

Twelve sequences shown by SEQ ID NO: 1 and 4 sequences of single base-substituted form were present. Five sequences (4 kinds) containing consensus sequence 1, which are included in the sequence shown by SEQ ID NO: 1, were present (SEQ ID NOs: 2-5).

Twelve sequences shown by SEQ ID NO: 6, 1 sequence of single base-substituted form, and 6 sequences of dibasic-substituted form were present.

Twelve sequences shown by SEQ ID NO: 7, 2 sequences of single base-substituted form, and 1 sequence of dibasic-substituted form were present.

One sequence containing consensus sequence 2, which is included in the sequence shown by SEQ ID NO: 7, was present (SEQ ID NO: 8).

Seven sequences shown by SEQ ID NO: 9, one sequence of single base-substituted form, and 2 sequences of dibasic-substituted form were present.

Four sequences shown by SEQ ID NO: 10 were present. Eight sequences (3 kinds) containing consensus sequence 3, which are included in the sequence shown by SEQ ID NO: 10, were present (SEQ ID NOs: 11-13).

Four sequences shown by SEQ ID NO: 14, and one sequence of single base-deleted form were present. Three sequences shown by SEQ ID NOs: 15-17 were present. Three sequences shown by SEQ ID NO: 18, and one sequence of dibasic variant were present. Two sequences shown by SEQ ID NOs: 19-20 were present. Two sequences shown by SEQ ID NO: 21, and one sequence of single base variant were present. Two sequences shown by SEQ ID NO: 22 and one sequence of dibasic variant were present. One sequence each of the sequences shown by SEQ ID NOs: 23-34 was present.

The secondary structures of the sequences shown by SEQ ID NOs: 1-5, which contain consensus sequence 1, were predicted by the MFOLD program (M. Zuker, Nucleic Acids Res. 31(13), 3406-3415, 2003). As a result, the shape of the consensus sequence part was similar (see FIG. 1).

The secondary structures of the sequences shown by SEQ ID NOs: 7 and 8, which contain consensus sequence 2, were predicted by the MFOLD program. As a result, the shape of the consensus sequence part was loop (see FIG. 2).

The secondary structures of the sequences shown by SEQ ID NOs: 10-13, which contain consensus sequence 3, were predicted by the MFOLD program. As a result, the shape of the consensus sequence part was the same (see FIG. 3).

These sequences are different from the sequences of the nucleic acid ligands described in the aforementioned patent document 2, patent document 5 and patent document 6.

Respective nucleotide sequences are shown below. The parentheses in each nucleotide show modifications at the 2'-position of ribose and F is a fluorine atom. Specifically, c(F) is cytidine wherein the 2'-position of ribose is substituted by a fluorine atom, and u(F) is uridine wherein the 2'-position of ribose is substituted by a fluorine atom.

The beginning of each sequence is 5' terminal and the end is 3' terminal.

```
SEQ ID NO: 1:
gggc(F)u(F)u(F)gu(F)u(F)c(F)u(F)ggau(F)c(F)gc(F)c(F)gu(F)u(F)a aau(F)gu(F)c(F)u(F)agu(F)agu(F)ac(F)u(F)au(F)u(F)c(F)au(F)gu(F)

u(F)u(F)ac(F)ggau(F)u(F)gc(F)ggc(F)gau(F)gc(F)u(F)c(F)agaagc (F)ggag

SEQ ID .NO: 2:
gggc(F)u(F)u(F)gu(F)u(F)c(F)u(F)ggau(F)c(F)gc(F)c(F)u(F)ggaau (F)agau(F)agagu(F)agu(F)ac(F)u(F)u(F)au(F)aggu(F)u(F)u(F)ac(F)c (F)u(F)gu(F)gau(F)ggc(F)gau(F)gc(F)u(F)c(F)agaagc(F)ggag SEQ ID NO: 3:
gggc(F)u(F)u(F)gu(F)u(F)c(F)u(F)ggau(F)c(F)gc(F)c(F)u(F)u(F)u (F)u(F)agu(F)agu(F)ac(F)u(F)gu(F)u(F)aau(F)gu(F)u(F)u(F)ac(F)ga aagggu(F)u(F)u(F)ggc(F)u(F)ggc(F)gau(F)gc(F)u(F)c(F)agaagc(F)g gag SEQ ID NO: 4:
gggc(F)u(F)u(F)gu(F)u(F)c(F)u(F)ggau(F)c(F)gc(F)c(F)au(F)gc(F)

gagu(F)aguac(F)u(F)aau(F)c(F)au(F)gu(F)u(F)u(F)ac(F)c(F)gau(F)

gu(F)gggu(F)ggc(F)ggc(F)gau(F)gc(F)u(F)c(F)agaagc(F)ggag
```

-continued

SEQ ID NO: 5:
gggc(F)u(F)u(F)gu(F)u(F)c(F)u(F)ggau(F)c(F)gc(F)c(F)u(F)gggau (F)ggu(F)u(F)u(F)c(F)agu(F)agu(F)ac(F)u(F)au(F)aggu(F)u(F)u (F)ac(F)ggaggagggc(F)gau(F)gc(F)u(F)c(F)agaagc(F)ggag SEQ ID NO: 6:
gggc(F)u(F)u(F)gu(F)u(F)c(F)u(F)ggau(F)c(F)gc(F)c(F)u(F)u(F)ac (F)gau(F)u(F)agaggau(F)au(F)u(F)au(F)u(F)ac(F)u(F)c(F)

gau(F)u(F)gu(F)u(F)ggggc(F)gau(F)gc(F)u(F)c(F)agaagc(F)ggag

SEQ ID NO: 7:
gggc(F)u(F)u(F)gu(F)u(F)c(F)u(F)ggau(F)c(F)gc(F)c(F)u(F)gau(F)

aagc(F)aggagggu(F)gac(F)ggu(F)gau(F)ggc(F)agc(F)u(F)gu(F)u(F)u (F)ggggc(F)gau(F)gc(F)u(F)c(F)agaagc(F)ggag SEQ ID NO: 8:
gggc (F)u(F)u(F)gu(F)u(F)c(F)u(F)ggau(F)c(F)gc(F)ggagagu(F)u(F)

gu(F)c(F)gagggu(F)gac(F)ggu(F)au(F)agc(F)aggac(F)gc(F)u(F)gu(F)

u(F)u(F)ggc(F)gau(F)gc(F)u(F)c(F)agaagc(F)ggag

SEQ ID NO: 9:
gggc(F)u(F)u(F)gu(F)u(F)c(F)u(F)ggau(F)c(F)gc(F)gau(F)gc(F)aag u(F)u(F)ac(F)c(F)agu(F)gu(F)agc(F)u(F)agu(F)u(F)ac(F)u(F)agggc (F)gu(F)gu(F)gu(F)u(F)ggc(F)gau(F)gc(F)u(F)c(F)agaagc(F)ggag SEQ ID NO: 10:
gggc(F)u(F)u(F)gu(F)u(F)c(F)u(F)ggau(F)c(F)gc(F)u(F)c(F)gu(F)u (F)gac(F)u(F)agggc(F)gu(F)ac(F)au(F)c(F)gu(F)gac(F)c(F)agu(F)g u(F)c(F)agu(F)u(F)c(F)agggc(F)gau(F)gc(F)u(F)c(F)agaagc(F)ggag SEQ ID NO: 11:
gggc(F)u(F)u(F)gu(F)u(F)c(F)u(F)ggau(F)c(F)gc(F)au(F)c(F)agu(F)

ac(F)u(F)agggc(F)u(F)c(F)u(F)u(F)aggagu(F)gac(F)c(F)agu(F)gu(F)

gu(F)u(F)gu(F)aaggc(F)gau(F)gc(F)u(F)c(F)agaagc(F)ggag

SEQ ID NO: 12:
gggc(F)u(F)u(F)gu(F)u(F)c(F)u(F)ggau(F)c(F)gc(F)u(F)gc(F)u(F)a gggc(F)gc(F)au(F)u(F)u(F)ac(F)u(F)u(F)gc(F)gu(F)u(F)ac(F)c(F)a gu(F)gc(F)ggc(F)ggu(F)gu(F)ggc(F)gau(F)gc(F)u(F)c(F)agaagc(F)g gag SEQ ID NO: 13:
gggc(F)u(F)u(F)gu(F)u(F)c(F)u(F)ggau(F)c(F)gc(F)u(F)ggc(F)u(F)

c(F)gac(F)ac(F)u(F)agggc(F)c(F)gagggu(F)u(F)ac(F)c(F)agu(F)gu (F)gu(F)u(F)aagu(F)aggc(F)gau(F)gc(F)u(F)c(F)agaagc(F)ggag SEQ ID NO: 14:
gggc(F)u(F)u(F)gu(F)u(F)c(F)u(F)ggau(F)c(F)gc(F)ac(F)c(F)agaag u(F)u(F)u(F)c(F)u(F)u(F)gc(F)u(F)gac(F)c(F)gagu(F)aggu(F)u(F)g gggau(F)gu(F)c(F)u(F)ggc(F)gau(F)gc(F)u(F)c(F)agaagc(F)ggag SEQ ID NO: 15:
gggc(F)u(F)u(F)gu(F)u(F)c(F)u(F)ggau(F)c(F)gc(F)c(F)ggu(F)au(F)

au(F)aaaau(F)gu(F)c(F)u(F)u(F)u(F)gac(F)gggu(F)gc(F)gu(F)c(F)

u(F)ggu(F)c(F)ggu(F)aggc(F)gau(F)gc(F)u(F)c(F)agaagc(F)ggag

SEQ ID NO: 16:
gggc(F)u(F)u(F)gu(F)u(F)c(F)u(F)ggau(F)c(F)gc(F)c(F)u(F)gu(F)u (F)au(F)gu(F)u(F)u(F)agaac(F)u(F)u(F)ggu(F)u(F)u(F)u(F)agg agu(F)c(F)gac(F)au(F)gggggc(F)gau(F)gc(F)u(F)c(F)agaagc(F)ggag SEQ ID NO: 17:
gggc(F)u(F)u(F)gu(F)u(F)c(F)u(F)ggau(F)c(F)gc(F)c(F)c(F)u( F).u(F)gau(F)c(F)aau(F)gggu(F)c(F)aagaau(F)u(F)u(F)c(F)gc(F)aac (F)u(F)c(F)c(F)gggc(F)gu(F)ggc(F)gau(F)gc(F)u(F)c(F)agaagc(F)g gag SEQ ID NO: 18:
gggc(F)u(F)u(F)gu(F)u(F)c(F)u(F)ggau(F)c(F)gc(F)u(F)u(F)u(F)ga u(F)ggau(F)gc(F)au(F)u(F)c(F)c(F)aac(F)u(F)au(F)u(F)gau(F)u(F)

u(F)gu(F)u(F)gggau(F)c(F)c(F)ggc(F)gau(F)gc(F)u(F)c(F)agaa gc(F)ggag

SEQ ID NO: 19:
gggc(F)u(F)u(F)gu(F)u(F)c(F)u(F)ggau(F)c(F)gc(F)gc(F)ggu(F)aga u(F)c(F)aau(F)aagau(F)u(F)au(F)u(F)gu(F)u(F)c(F)ggu(F)aggaagau (F)u(F)gu(F)ggc(F)gau(F)gc(F)u(F)c(F)agaagc(F)ggag SEQ ID NO: 20:
gggc(F)u(F)u(F)gu(F)u(F)c(F)u(F)ggau(F)c(F)gc(F)c(F)gu(F)u (F)c(F)aau(F)u(F)gc(F)au(F)gu(F)u(F)ggaagau(F)gc(F)au(F)gu(F)u (F)u(F)c(F)u(F)u(F)gu(F)u(F)c(F)gggc(F)gau(F)gc(F)u(F)c(F)agaa gc(F)ggag SEQ ID NO: 21:
gggc(F)u(F)u(F)gu(F)u(F)c(F)u(F)ggau(F)c(F)gc(F)c(F)u(F)ac(F)u (F)au(F)aau(F)ac(F)gu(F)u(F)au(F)u(F)gagu(F)ggc(F)gc(F)au(F)au (F)u(F)u(F)u(F)u(F)gu(F)gu(F)aggc(F)gau(F)gc(F)u(F)c(F)agaagc(F)

ggag

SEQ ID NO: 22:
gggc(F)u(F)u(F)gu(F)u(F)c(F)u(F)ggau(F)c(F)gc(F)agc(F)gaau(F)g gu(F)u(F)u(F)gu(F)u(F)gu(F)u(F)c(F)gc(F)agu(F)ac(F)u(F)au(F)u(F)

u(F)agu(F)gc(F)u(F)u(F)u(F)gggc(F)gau(F)gc(F)u(F)c(F)agaagc(F)

ggag

SEQ ID NO: 23:
gggc(F)u(F)u(F)gu(F)u(F)c(F)u(F)ggau(F)c(F)gc(F)ggu(F)ggau(F)a u(F)gu(F)u(F)c(F)u(F)au(F)c(F)c(F)aaau(F)gu(F)aau(F)aau(F)u(F)

u(F)gu(F)ac(F)u(F)au(F)ggc(F)gau(F)gc(F)u(F)c(F)agaagc(F)ggag

SEQ ID NO: 24:
gggc(F)u(F)u(F)gu(F)u(F)c(F)u(F)ggau(F)c(F)gc(F)u(F)c(F)gu(F)g u(F)ac(F)u(F)aggu(F)gu(F)gu(F)c(F)gaaau(F)gu(F)u(F)agc(F)u(F)u (F)u(F)c(F)gc(F)gagagggc(F)gau(F)gc(F)u(F)c(F)agaagc(F)ggag SEQ ID NO: 25:
gggc(F)u(F)u(F)gu(F)u(F)c(F)u(F)ggau(F)c(F)gc(F)c(F)ggu(F)agu(F)

agaagaau(F)c(F)gau(F)u(F)u(F)au(F)gc(F)gu(F)au(F)gc(F)u(F)gg u(F)c(F)gu(F)u(F)aggc(F)gau(F)gc(F)u(F)c(F)agaagc(F)ggag -continued SEQ ID NO: 26:
gggc(F)u(F)u(F)gu(F)u(F)c(F)u(F)ggau(F)c(F)gc(F)au(F)au(F)u(F)

gagagau(F)gu(F)au(F)gac(F)u(F)u(F)u(F)u(F)aaggaac(F)aggu(F)u(F)

gu(F)u(F)gggc(F)gau(F)gc(F)u(F)c(F)agaagc(F)ggag

SEQ ID NO: 27:
gggc(F)u(F)u(F)gu(F)u(F)c(F)u(F)ggau(F)c(F)gc(F)c(F)au(F)u(F)a agc(F)aaagu(F)u(F)u(F)ggu(F)ac(F)u(F)au(F)gc(F)u(F)agu(F)aac(F)

u(F)gagau(F)au(F)ggc(F)gau(F)gc(F)u(F)c(F)agaagc(F)ggag

SEQ ID NO: 28:
gggc(F)u(F)u(F)gu(F)u(F)c(F)u(F)ggau(F)c(F)gc(F)ac(F)au(F)c(F)

ggggc(F)aaau(F)gu(F)u(F)u(F)au(F)u(F)u(F)ggaaac(F)aac(F)ggu(F)

c(F)u(F)u(F)u(F)gggc(F)gau(F)gc(F)u(F)c(F)agaagc(F)ggag

SEQ ID NO: 29:
gggc(F)u(F)u(F)gu(F)u(F)c(F)u(F)ggau(F)c(F)gc(F)c(F)u(F)agau(F)

u(F)u(F)u(F)u(F)u(F)u(F)u(F)u(F)agaggc(F)au(F)c(F)ac(F)u(F)gu (F)gau(F)u(F)u(F)u(F)gc(F)au(F)u(F)ggau(F)gu(F)ggc(F)gau(F)gc(F)

u(F)c(F)agaagc(F)ggag

SEQ ID NO: 30:
gggc(F)u(F)u(F)gu(F)u(F)c(F)u(F)ggau(F)c(F)gc(F)c(F)ggu(F)aau(F)

gu(F)gc(F)au(F)ac(F)ac(F)ac(F)u(F)au(F)u(F)gac(F)c(F)u(F)u(F)

aac(F)agau(F)u(F)gaggc(F)gau(F)gc(F)u(F)c(F)agaagc(F)ggag

Figure 4:
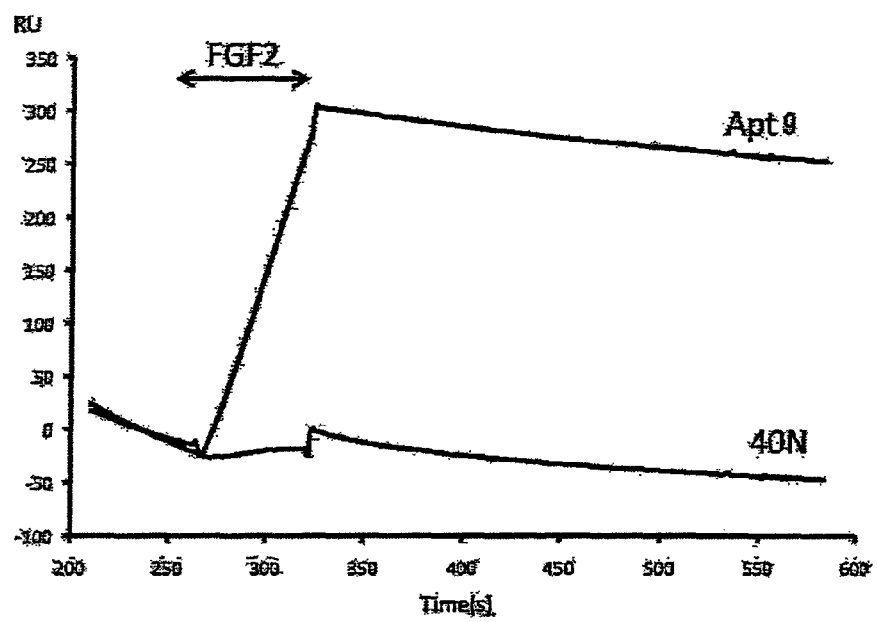
FIG. 4 is a sensorgram showing that the aptamer shown by SEQ ID NO: 9 (Apt9) binds to human FGF2.

SEQ ID NO: 31:
gggc(F)u(F)u(F)gu(F)u(F)c(F)u(F)ggau(F)c(F)gc(F)gc(F)gc(F)aaac (F)u(F)agu(F)u(F)aagc(F)u(F)agc(F)c(F)gau(F)c(F)ac(F)aggggu(F)

c(F)gc(F)au(F)u(F)ggc(F)gau(F)gc(F)u(F)c(F)agaagc(F)ggag

SEQ ID NO: 32:
gggc(F)u(F)u(F)gu(F)u(F)c(F)u(F)ggau(F)c(F)gc(F)u(F)ac(F)u(F)u (F)aac(F)ac(F)ac(F)u(F)ggu(F)aac(F)c(F)c(F)u(F)c(F)ggc(F)c(F)c (F)u(F)agu(F)gu(F)c(F)gagc(F)c(F)aggc(F)gau(F)gc(F)u(F)c(F)aga agc(F)ggag SEQ ID NO: 33:
gggc(F)u(F)u(F)gu(F)u(F)c(F)u(F)ggau(F)c(F)gc(F)c(F)c(F)au(F)a u(F)aggc(F)u(F)gu(F)u(F)c(F)c(F)gc(F)ggc(F)aau(F)agaau(F)u(F)u (F)gc(F)agu(F)u(F)au(F)u(F)gggc(F)gau(F)gc(F)u(F)c(F)agaagc(F)

ggag

SEQ ID NO: 34:
gggc(F)u(F)u(F)gu(F)u(F)c(F)u(F)ggau(F)c(F)gc(F)u(F)aagggu(F)u (F)u(F)gagu(F)c(F)u(F)u(F)au(F)c(F)u(F)ac(F)c(F)u(F)gc(F)u(F)g u(F)gc(F)aaau(F)gc(F)ggc(F)ggc(F)gau(F)gc(F)u(F)c(F)agaagc(F)g gag The binding activities for FGF2 of the nucleic acids shown by SEQ ID NOs:1, 6, 7, 9, 10 and 14-34 were evaluated by the surface plasmon resonance method. The measurements were taken using 2000 manufactured by BIAcore. The SA chip was used as the sensor chip, which had streptavidin immobilized thereon. Bound thereto was about 600 RU of a 16-nucleotide Poly dT with biotin bound to the 5' end thereof. The ligand nucleic acid had a 16-nucleotide Poly A added to the 3' end thereof, and was immobilized on the SA chip via a bond between dT and A. The amount immobilized was about 1000 RU. 20 μL of human FGF2 for analyte, prepared at 0.5 μM, was injected, with the m addition of a 0.5 mg/mL tRNA to lessen nonspecific adsorption. Solution A was used as a running buffer. As a result of the measurement, it was found that all of the nucleic acids shown by SEQ ID NOs:1, 6, 7, 9, 10 and 14-34 bind to FGF2 significantly more than the negative control 40N. Here, 40N refers to the nucleic acid pool used for the first round of SELEX, comprising a 40-nucleotide random sequence. As an example, a sensorgram showing a status of the binding of the aptamer shown by SEQ ID NO:1 (Apt1) and human FGF2 is shown in FIG. 4. From the above, it was shown that the nucleic acids shown by SEQ ID NOs:1, 6, 7, 9, 10 and 14-34 are aptamers that bind to FGF2.

Figure 5:
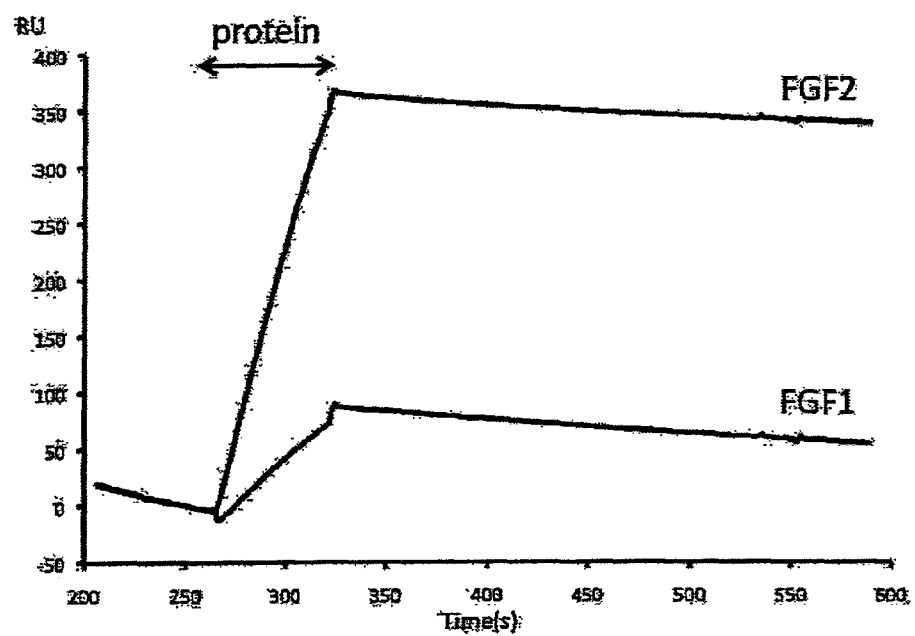
FIG. 5 is a sensorgram showing that the aptamer shown by SEQ ID NO: 9 (Apt9) does not bind to human FGF1.

Whether the FGF2 aptamers shown by SEQ ID NOs:1, 6, 7, 9, 10 and 14-34 bind to FGF1 in the same FGF family was evaluated by the surface plasmon resonance method. In the experiment, FGF1 (232-FA/CF) manufactured by R&D Systems was used, and the experiment was performed by adding tRNA to reduce non-specific adsorption as in the above. As a result, it was found that none of the aptamers shown by SEQ ID NOs: 1-5 and 26-33 were bound to FGF1. As one embodiment, a sensorgram showing that the aptamer shown by SEQ ID NO: 11 does not bind to human FGF1 is shown in FIG. 5. From the above, it was found that the aptamers shown by SEQ ID NOs: 1, 6, 7, 9, 10, 14-34 specifically bind to FGF2.

Example 2

Aptamers that Inhibit the Binding of FGF2 and an FGF2 Receptor

Figure 6:
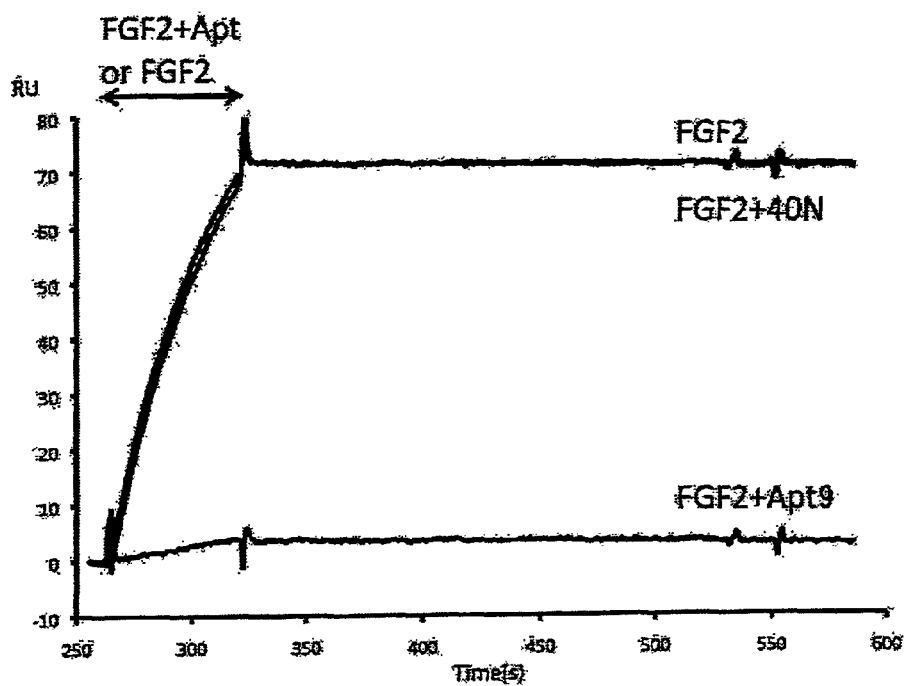
FIG. 6 is a sensorgram showing that the aptamer shown by SEQ ID NO: 9 (Apt9) inhibits binding of human FGF2 and a human FGF2 receptor.

Whether the aptamers shown by SEQ ID NOs:1, 6, 7 and 9-11 inhibit the binding of FGF2 and an FGF2 receptor (FGFR1C) was determined using the surface plasmon resonance method. As directed in BIAcore Company's protocol, Protein A (21181, PIERCE) was immobilized on a CM5 sensor chip. About 500 RU of human FGFR1C-Fc fused with the Fc portion of IgG (658-FR, R&D systems) was immobilized thereon. As the analyte, a mixture of FGF2 (0.1 µM) and each aptamer (0.3 µM) was mixed, retained for minutes and injected. If the aptamer inhibits the binding of FGF2 and an FGF2 receptor, the signal on the sensorgram is expected to not rise; if the aptamer does not inhibit the binding, a triple complex will be formed and the signal is expected to rise. Before starting the inhibition experiment, binding of FGF2 and an FGF2 receptor was confirmed. As a negative control, a mixture of FGF2 and 40N was used. 40N is a nucleic acid pool used for the first round of SELEX, which contains 40 nucleotide random sequence. As a result of the experiment, all the aptamers shown by SEQ ID NOs: 1, 6, 7 and 9-11 were found to inhibit the binding of FGF2 and an FGF2 receptor. Particularly, the inhibitory effect of the aptamers shown by SEQ ID NOs: 9-11 was high. On the other hand, 40N did not show an inhibitory activity. As one embodiment, a sensorgram showing that the aptamer shown by SEQ ID NO: 9 inhibits binding of FGF2 and an FGF2 receptor is shown in FIG. 6.

From the above, it was shown that the aptamers shown by SEQ ID NOs: 1, 6, 7, 9-11 can be used as FGF2 inhibitors.

Example 3

Aptamer Inhibits FGF2 Signaling of Cultured Cells

Whether the aptamers shown by SEQ ID NOs: 1, 6, 7, 9-11 can inhibit cell stimulation by FGF2 was confirmed using mouse fibroblast (NIH3T3). With cell stimulation by FGF2, the signal transduction system of NIH3T3 cell is activated, which activates MAP kinase pathway, PIK3/AKT1 pathway and the like via FRS2, Grb2, SOS, which finally induces expression of various cytokine and receptor genes such as VEGF-A, VEGF-C, HGF, angiopoietin-2, VEGFR, PDGFR-α and the like. It has been elucidated that factors such as FRS2, ERK (Extracellular Signal-regulated Kinase) and the like are phosphorylated during the process. When NIH3T3 cell was stimulated by human FGF2 (manufactured by Peprotech) (50 ng/ml), aptamer was added to the medium, and the measurement was performed 30 min later by Western blotting. As the antibody, a phosphorylation-specific antibody (P-FRS2-alpha Y196, P-ERK T202/Y204; Cell signaling technology) was used. The inhibitory effect of the aptamer on FGF2 signaling is shown in FIG. 7. The aptamers shown by SEQ ID NOs: 7, 9-11 strongly inhibited phosphorylation of FRS2 and ERK. The strong inhibitory effect by the aptamers shown by SEQ ID NOs: 9-11 matched with the inhibitory results on the binding of FGF2 and an FGF2 receptor by the plasmon resonance method. The above has shown that the aptamers shown by SEQ ID NOs: 7, 9-11 of the present invention have a high inhibitory activity on FGF2 signaling even in viable cells.

Example 4

Shortening of Aaptamers shown by SEQ ID NOs: 7, 9-11

Figure 8:
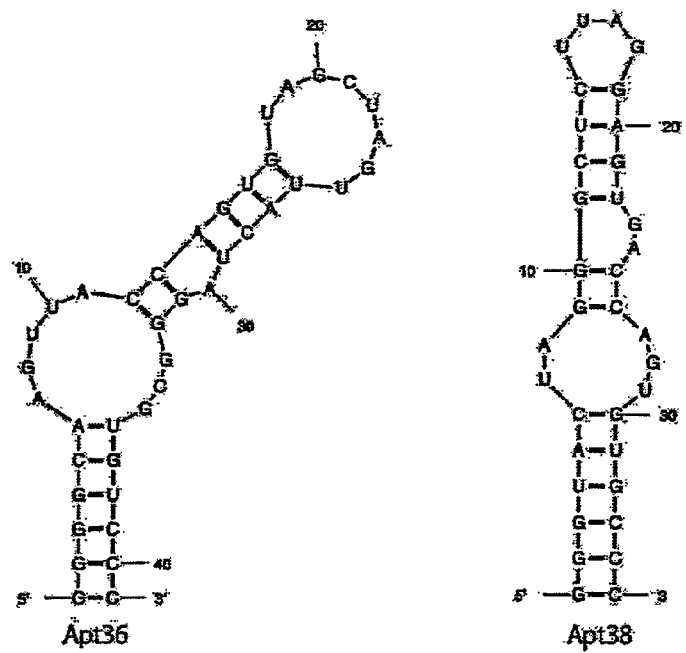
FIG. 8 shows the secondary structures of the shortened aptamers shown by SEQ ID NO: 36 and 38 predicted by the MFOLD program.

The aptamers shown by SEQ ID NOs: 7, 9-11 were shortened, and whether these nucleic acids have an inhibitory activity on the binding of FGF2 and an FGF2 receptor was examined by the surface plasmon resonance method, in the same manner as in Example 2. The nucleic acids shown by SEQ ID NOs: 35-38 were obtained by in vitro transcription reaction using DuraScribe (trademark) T7 Transcription Kit (manufactured by Epicentre). As a result, the aptamers shown by SEQ ID NOs: 36, 38 had an inhibitory activity on the binding of FGF2 and an FGF2 receptor even after shortening. The secondary structures of the shortened aptamers shown by SEQ ID NOs: 36 and 38 as predicted by the MFOLD program are shown in FIG. 8.

SEQ ID NO: 35: 38 nucleotide aptamer which is an alteration of the aptamer shown by SEQ ID NO: 7
gggaagc(F)aggagggu(F)gac(F)ggu(F)gau(F)ggc(F)agc(F)u(F)gu(F)u(F)u (F)c(F)c(F)c(F)

SEQ ID NO: 36: 41 nucleotide aptamer which is an alteration of the aptamer shown by SEQ ID NO: 9
ggggc(f)aagu(f)u(f)ac(f)c(f)agu(f)gu(f)agc(f)u(f)agu(f)u(f)ac(f)u(f)agggc(f)gu(f)gu(f)c(f) c(f)c(f)

SEQ ID NO: 37: 47 nucleotide aptamer which is an alteration of the aptamer shown by SEQ ID NO: 10
gggau(F)cgc(F)u(F)c(F)gu(F)u(F)gac(F)u(F)agggc(F)gu(F)ac(F)au(F)cgu (F)gac(F)c(F)agu(F)gu(F)c(F)agu(F)c(F)c(F)c(F)

SEQ ID NO: 38: 35 nucleotide aptamer which is an alteration of the aptamer shown by SEQ ID NO: 11
gggu(F)ac(F)u(F)agggc(F)u(F)c(F)u(F)u(F)aggagu(F)gac (F)c(F)agu (F)gu(F)gc(F)c(F)c(F)

Example 5

Shortened Aptamer Inhibits FGF2 Signaling of Cultured Cells

Whether the aptamers shown by SEQ ID NOs: 36, 38 can inhibit cell stimulation by FGF2 was confirmed using mouse fibroblast (NIH3T3), in the same manner as in Example 3. As a result, the aptamers shown by SEQ ID NOs: 36, 38 strongly inhibited phosphorylation of FRS2 and ERK (FIG. 9). It has been shown that these shortened aptamers have a high inhibitory activity on FGF2 signaling in living cells, like the aptamers shown by SEQ ID NOs: 9, 11.

Example 6

Production of a Variant of the Aptamer shown by SEQ ID NO: 36

A variant of the aptamer shown by SEQ ID NO: 36 was produced by the SELEX method. SELEX was performed in the same manner as in Example 1 and using a DNA template obtained by artificially mutating the aptamer sequence shown by SEQ ID NO: 36. As a target substance, human FGF2 (manufactured by Peprotech) was used.

RNA used in the first round was obtained by transcribing a DNA, obtained by chemical synthesis, using a DuraScribe (trademark) T7 Transcription Kit (manufactured by Epicentre). RNA obtained by this method is that wherein the 2'-position of the ribose of a pyrimidine nucleotide is fluorinated. As a DNA template, 100 nucleotide DNA having primer sequences at both ends, which is shown below, was used. The DNA template and primer were produced by chemical synthesis. The DNA template and primer used are shown below. The underlined portion was synthesized to be substituted by other bases at a proportion of 30%.

```
DNA templates:
                                        (SEQ ID NO: 58)
5'-taatacgactcactatagggaagaggtcagatggggcgatgcaag ttaccagtgtagctagttactagggcgtgtgttgccccctatgcgtgct agagtga-3' primer Fwd:
                                        (SEQ ID NO: 59)
5'-taatacgactcactatagggaagaggtcagat-3' primer Rev:
                                        (SEQ ID NO: 60)
5'-tcactctagcacgcata-3'
```

SELEX was performed 10 rounds, and the PCR products were cloned into pGEM-T Easy vector, which was used to transform *Escherichia coli* strain DH5a. The plasmid was extracted from a single colony, and the base sequences of 41 clones were examined by a DNA sequencer.

After 10 rounds of SELEX, the sequences showed convergence. While a sequence identical to the aptamer shown by SEQ ID NO: 36 did not exist, a sequence common to all sequences was present (SEQ ID NO: 42; consensus sequence 4). Twenty sequences shown by SEQ ID NO: 43 were present. Five sequences shown by SEQ ID NO: 44 were present. Three sequences shown by SEQ ID NO: 45 were present. Two sequences shown by SEQ ID NO: 46 were present. One sequence each of the sequences shown by SEQ ID NOs: 47-57 was present.

The secondary structure of the sequences shown by SEQ ID NOs: 43-46, which contain the consensus sequence 4 shown by SEQ ID NO: 42, was predicted using MFOLD program. As a result, the shape of the consensus sequence 4 part was similar (see FIG. 10).

Each nucleotide sequence is shown below. The parentheses in each nucleotide show modification of the 2'-position of ribose. F shows a fluorine atom. Specifically, c(F) shows cytidine wherein the 2'-position of ribose is substituted by a fluorine atom, and u(F) shows uridine wherein the 2'-position of ribose is substituted by a fluorine atom.

In addition, the beginning of each sequence is 5'terminal and the end is 3'terminal.

```
SEQ ID NO: 42:
gu(F)u(F)ac(F)c(F)agu(F)gu(F)nnnnnnnnnnnagggc(F)

SEQ ID NO: 43:
gggaagaggu(F)c(F)agau(F)ggu(F)u(F)c(F)c(F)c(F)c(F)gc(F)ac(F)gu (F)u(F)ac(F)c(F)agu(F)gu(F)agaaaac(F)u(F)ac(F)u(F)agggc(F)gu(F)

gu(F)gau(F)c(F)ac(F)c(F)c(F)u(F)au(F)gc(F)gu(F)gc(F)u(F)agagu (F)ga

SEQ ID NO: 44:
gggaagaggu(F)c(F)agau(F)ggc(F)c(F)c(F)gc(F)c(F)u(F)c(F)ac(F)gu (F)u(F)ac(F)c(F)agu(F)gu(F)gagu(F)u(F)gu(F)c(F)ac(F)c(F)agggc (F)gu(F)gu(F)gu(F)u(F)gcac(F)c(F)u(F)au(F)gc(F)gu(F)gc(F)u(F)ag agu(F)ga SEQ ID NO: 45:
gggaagaggu(F)c(F)agau(F)ggc(F)c(F)u(F)u(F)c(F)c(F)gc(F)aggu(F)

u(F)ac(F)c(F)agu(F)gu(F)agu(F)u(F)u(F)aau(F)ac(F)u(F)agggc(F)c (F)u(F)gu(F)au(F)u(F)gc(F)ac(F)c(F)u(F)u(F)au(F)gc(F)gu(F)gc(F)

u(F)agagu(F)ga

SEQ ID NO: 46:
gggaagaggu(F)c(F)agau(F)ggggac(F)c(F)u(F)u(F)ggcgu(F)u(F)ac(F)

c(F)agu(F)gu(F)aggaaac(F)u(F)ac(F)u(F)agggc(F)gc(F)gu(F)gu(F)a gc(F)ac(F)c(F)u(F)au(F)gc(F)gu(F)gc(F)u(F)agagu(F)gau(F)au(F)g c(F)gu(F)gc(F)u(F)agagu(F)ga
```

SEQ ID NO: 47:
gggaagaggu(F)c(F)agau(F)ggu(F)u(F)c(F)c(F)c(F)gc(F)ac(F)gu(F)u(F)ac(F)c(F)agu(F)gu(F)agaaaac(F)u(F)ac(F)u(F)agggc(F)gu(F)gu(F)aau(F)gc(F)ac(F)c(F)u(F)u(F)au(F)gc(F)gu(F)gc(F)u(F)agagu(F)ga SEQ ID NO: 48:
gggaagaggu(F)c(F)agau(F)ggc(F)u(F)c(F)c(F)c(F)gc(F)ac(F)gu(F)gac(F)c(F)agu(F)gu(F)agu(F)u(F)aac(F)u(F)ac(F)u(F)agggc(F)gu(F)gu(F)gaagc(F)ac(F)c(F)u(F)au(F)u(F)gc(F)gu(F)gc(F)u(F)agagu(F)ga SEQ ID NO: 49:
gggaagaggu(F)c(F)agau(F)ggu(F)u(F)c(F)c(F)c(F)c(F)gc(F)ac(F)gu(F)u(F)ac(F)c(F)agu(F)gu(F)agau(F)agau(F)ac(F)u(F)agggc(F)gu(F)gu(F)u(F)u(F)agc(F)ac(F)c(F)u(F)u(F)au(F)gc(F)gu(F)gc(F)u(F)agagu(F)ga SEQ ID NO: 50:
gggaagaggu(F)c(F)agau(F)gggc(F)c(F)u(F)c(F)c(F)ac(F)aagu(F)u(F)ac(F)c(F)agu(F)gu(F)agc(F)gc(F)au(F)u(F)ac(F)u(F)agggc(F)u(F)u(F)gu(F)gc(F)u(F)c(F)ac(F)c(F)u(F)au(F)gc(F)gu(F)gc(F)u(F)agagu(F)ga SEQ ID NO: 51:
gggaagaggu(F)c(F)agau(F)ggau(F)c(F)u(F)c(F)u(F)gc(F)ac(F)gu(F)u(F)ac(F)c(F)agu(F)gu(F)au(F)gu(F)aau(F)u(F)ac(F)u(F)agggc(F)gu(F)gu(F)gu(F)u(F)gc(F)ac(F)c(F)u(F)au(F)gc(F)gu(F)gc(F)u(F)agagu(F)ga SEQ ID NO: 52:
gggaagaggu(F)c(F)agau(F)ggau(F)c(F)u(F)c(F)u(F)gc(F)ac(F)gu(F)u(F)ac(F)c(F)agu(F)gu(F)aagu(F)u(F)gu(F)u(F)ac(F)u(F)agggc(F)gu(F)gu(F)gu(F)u(F)gc(F)ac(F)c(F)u(F)au(F)gc(F)gu(F)gc(F)u(F)agagu(F)ga SEQ ID NO: 53:
gggaagaggu(F)c(F)agau(F)ggc(F)u(F)u(F)c(F)c(F)u(F)gc(F)ac(F)gu(F)u(F)ac(F)c(F)au(F)u(F)gu(F)au(F)gu(F)u(F)gu(F)u(F)ac(F)u(F)agggc(F)gu(F)ggc(F)u(F)u(F)gc(F)ac(F)c(F)u(F)au(F)gc(F)gu(F)gc(F)u(F)agagu(F)ga SEQ ID NO: 54:
gggaagaggu(F)c(F)agau(F)ggac(F)u(F)u(F)c(F)u(F)gc(F)ac(F)gu(F)u(F)ac(F)c(F)agu(F)gu(F)agc(F)u(F)au(F)u(F)u(F)ac(F)c(F)agggc(F)gu(F)gu(F)gu(F)agc(F)ac(F)c(F)u(F)au(F)gc(F)gu(F)gc(F)u(F)agagu(F)ga SEQ ID NO: 55:
gggaagaggu(F)c(F)agau(F)ggac(F)ac(F)c(F)u(F)gc(F)ac(F)gu(F)u(F)ac(F)c(F)agu(F)gu(F)aac(F)u(F)u(F)gu(F)u(F)ac(F)u(F)agggc(F)gu(F)gu(F)gu(F)agc(F)ac(F)c(F)u(F)au(F)gc(F)gu(F)gc(F)u(F)agagu(F)ga -continued SEQ ID NO: 56:
gggaagaggu(F)c(F)agau(F)ggc(F)u(F)u(F)c(F)c(F)u(F)aC(F)aagu(F)

u(F)ac(F)c(F)agu(F)gu(F)au(F)u(F)u(F)agu(F)u(F)ac(F)u(F)agggc (F)u(F)u(F)gu(F)gu(F)ggc(F)ac(F)c(F)u(F)au(F)gc(F)gu(F)gc(F)u(F)

agagu(F)ga

SEQ ID NO: 57:
gggaagaggu(F)c(F)agau(F)ggu(F)c(F)c(F)u(F)c(F)u(F)ac(F)aggu(F)

u(F)ac(F)c(F)agu(F)gu(F)au(F)u(F)au(F)u(F)u(F)ac(F)u(F)agg gc(F)c(F)u(F)gu(F)gu(F)u(F)gc(F)ac(F)c(F)u(F)au(F)gc(F)gu(F)gc (F)u(F)agagu (F)ga Whether the aptamers shown by SEQ ID NOs: 43-57 have an inhibitory activity on the binding of FGF2 and an FGF2 receptor was examined by the surface plasmon resonance in the same manner as in Example 2. The nucleic acids shown by SEQ ID NOs: 43-57 were obtained by in vitro transcription reaction using a DuraScribe (trademark) T7 Transcription Kit (manufactured by Epicentre). As a result, the aptamers shown by SEQ ID NOs: 43-57 were found to have an inhibitory activity on the binding of FGF2 and an FGF2 receptor.

INDUSTRIAL APPLICABILITY

The aptamer and complex of the present invention can be useful as medicaments, diagnostic reagents or reagents for diseases such as inflammatory disease, cancer, allergy, infection and the like. The aptamer and complex of the present invention can also be useful for the purification and concentration of FGF2, labeling of FGF2, as well as detection and quantification of FGF2.

This application is based on a patent application No. 2010-029377 filed in Japan, the contents of which are incorporated in full herein.

The invention claimed is:

1. An aptamer that binds to FGF2, which inhibits binding of FGF2 and an FGF2 receptor but does not inhibit binding of FGF1 and an FGF1 receptor, which comprises the sequence shown by SEQ ID NO: 36.

2. The aptamer according to claim 1, wherein a pyrimidine nucleotide of the aptamer is a modified nucleotide.

3. An aptamer that binds to FGF2, which inhibits binding of FGF2 and an FGF2 receptor but does not inhibit binding of FGF1 and an FGF1 receptor, which comprises:
 a nucleotide sequence selected from SEQ ID NOs: 36 and 43-57 wherein uracil may be thymine, and wherein,
 (i) the 2'-position of ribose of each pyrimidine nucleotide of the aptamer is the same or different and is a fluorine atom, or is substituted by a hydrogen atom, a hydroxy group and or a methoxy group,
 (ii) the 2'-position of ribose of each purine nucleotide of the aptamer is the same or different, and is a hydroxy group, or is substituted by a hydrogen atom, a methoxy group or a fluorine atom.

4. The aptamer according to claim 3, wherein a nucleotide of the aptamer is modified.

5. A complex comprising the aptamer according to claim 1 and a functional substance, wherein the functional substance is an affinity substance, a labeling substance, an enzyme, a drug delivery vehicle or a drug.

6. A medicament comprising the aptamer according to claim 3 or a complex comprising the aptamer according to claim 3 and a functional substance, wherein the functional substance is an affinity substance, a labeling substance, an enzyme, a drug delivery vehicle or a drug.

7. The medicament according to claim 6, which is for the treatment or prophylaxis of cancer, an autoimmune disease, an allergic disease, an inflammatory disease, heart dysplasia, angiodysplasia or skeletal dysplasia.

8. A diagnostic reagent comprising the aptamer according to claim 3 or a complex comprising the aptamer according to claim 3 and a functional substance.

* * * * *

SEQUENCE LISTING

<160> NUMBER OF SEQ ID NOS: 63

<210> SEQ ID NO 1
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 1
gggcuuguuc uggaucgccg uuaaaugucu aguaguacua uucauguuua cggauugcgg      60
cgaugcucag aagcggag                                                   78

<210> SEQ ID NO 2
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 2
gggcuuguuc uggaucgccu ggaauagaua gaguaguacu uauagguuua ccugugaugg      60
cgaugcucag aagcggag                                                   78

<210> SEQ ID NO 3
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 3

```
gggcuuguuc uggaucgccu uuuaguagua cguuaaugu uuacgaaagg guuuggcugg       60
cgaugcucag aagcggag                                                   78

<210> SEQ ID NO 4
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 4
gggcuuguuc uggaucgcca ugcgaguagu acuaaucaug uuuaccgaug ggguggcgg      60 cgaugcucag aagcggag                                                   78

<210> SEQ ID NO 5
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 5
gggcuuguuc uggaucgccu gggaugguuu caguaguacu auagguuua cggaggaggg      60 cgaugcucag aagcggag                                                   78

<210> SEQ ID NO 6
<211> LENGTH: 76
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 6
gggcuuguuc uggaucgccu uacgauuaga ggauauuaua uuuacucgau uguuggggcg     60
augcucagaa gcggag                                                     76

<210> SEQ ID NO 7
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 7
gggcuuguuc uggaucgccu gauaagcagg agggugacgg ugauggcagc uguuuggggg     60
cgaugcucag aagcggag                                                   78

<210> SEQ ID NO 8
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 8
gggcuuguuc uggaucgcgg agaguugucg agggugacgg uauagcagga cgcuguuugg     60
cgaugcucag aagcggag                                                   78
```

<210> SEQ ID NO 9
<211> LENGTH: 79
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 9
gggcuuguuc uggaucgcga ugcaaguuac caguguagcu aguuacuagg gcguguuug      60 gcgaugcuca gaagcggag                                                 79

<210> SEQ ID NO 10
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 10
gggcuuguuc uggaucgcuc guugacuagg gcguacaucg ugaccagugu caguucaggg      60
cgaugcucag aagcggag                                                   78

<210> SEQ ID NO 11
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 11
gggcuuguuc uggaucgcau caguacuagg gcucuuagga gugaccagug uguuguaagg      60
cgaugcucag aagcggag                                                   78

<210> SEQ ID NO 12
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 12
gggcuuguuc uggaucgcug cuagggcgca uuuacuugcg uuaccagugc ggcggugugg      60
cgaugcucag aagcggag                                                   78

<210> SEQ ID NO 13
<211> LENGTH: 79
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 13
gggcuuguuc uggaucgcug gcucgacacu agggccgagg guuaccagug uguuaaguag      60
gcgaugcuca gaagcggag                                                  79

<210> SEQ ID NO 14
<211> LENGTH: 78

```
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 14
gggcuuguuc uggaucgcac cagaaguuuc uugcugaccg aguagguugg ggaugucugg    60
cgaugcucag aagcggag                                                 78

<210> SEQ ID NO 15
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 15
gggcuuguuc uggaucgccg guauauaaaa ugucuuugac gggugcgucu ggucgguagg    60
cgaugcucag aagcggag                                                 78

<210> SEQ ID NO 16
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 16
gggcuuguuc uggaucgccu guuauguuua gaacuugguu uuuaggaguc gacauggggg    60
cgaugcucag aagcggag                                                 78

<210> SEQ ID NO 17
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 17
gggcuuguuc uggaucgccc cuugaucaau gggucaagaa uuucgcaacu ccgggcgugg    60
cgaugcucag aagcggag                                                 78

<210> SEQ ID NO 18
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 18
gggcuuguuc uggaucgcuu ugauggaugc auccaacua uugauuuguu gggauuccgg    60
cgaugcucag aagcggag                                                 78

<210> SEQ ID NO 19
<211> LENGTH: 78
<212> TYPE: RNA
<213> ORGANISM: Artificial
<220> FEATURE:
<223> OTHER INFORMATION: synthetic construct; nucleic acid having
``` binding activity against FGF-2

<400> SEQUENCE: 19
gggcuuguuc uggaucgcgc gguagaucaa uaagauuauu guucgguagg aagauugugg    60
cgaugcucag aagcggag                                                 78

<210> SEQ ID NO 20
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 20
gggcuuguuc uggaucgccu guucaauugc auguuggaag augcauguuu cuuguucggg    60
cgaugcucag aagcggag                                                 78

<210> SEQ ID NO 21
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 21
gggcuuguuc uggaucgccu acauaaauac guuauugagu ggcgcauauu uuuguguagg    60
cgaugcucag aagcggag                                                 78

<210> SEQ ID NO 22
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 22
gggcuuguuc uggaucgcag cgaauggnuu guuguucgca guacuauuua gugcuuggg    60 cgaugcucag aagcggag                                                 78

<210> SEQ ID NO 23
<211> LENGTH: 77
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 23
gggcuuguuc uggaucgcgg uggauauguu cuauccaaau guaauaauuu guacuauggc    60
gaugcucaga agcggag                                                  77

<210> SEQ ID NO 24
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 24

```
gggcuuguuc uggaucgcuc guguacuagg ugugucgaaa uguuagcuuu cgcgagaggg    60
cgaugcucag aagcggag                                                 78

<210> SEQ ID NO 25
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 25
gggcuuguuc uggaucgccg guaguagaag aaucgauuua ugcguaugcu ggucguuagg    60
cgaugcucag aagcggag                                                 78

<210> SEQ ID NO 26
<211> LENGTH: 77
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 26
gggcuuguuc uggaucgcau auugagagau guaugacuuu uaaggaacag guuguugggc    60
gaugcucaga agcggag                                                  77

<210> SEQ ID NO 27
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 27
gggcuuguuc uggaucgcca uuaagcaaag uuugguacua ugcuaguaac ugagauaugg    60
cgaugcucag aagcggag                                                 78

<210> SEQ ID NO 28
<211> LENGTH: 77
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 28
gggcuuguuc uggaucgcac aucggggcaa auguuuauuu ggaaacaacg gucuuugggc    60
gaugcucaga agcggag                                                  77

<210> SEQ ID NO 29
<211> LENGTH: 83
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 29
gggcuuguuc uggaucgccu agauuuuuuu uuagaggcau cacugugauu uugcauugga    60
uguggcgaug cucagaagcg gag                                           83
```

<210> SEQ ID NO 30
<211> LENGTH: 77
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 30
gggcuuguuc uggaucgccg guaaugugca uacacacuau ugaccuuaac agauugaggc    60
gaugcucaga agcggag                                                  77

<210> SEQ ID NO 31
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 31
gggcuuguuc uggaucgcgc gcaaacuagu uaagcuagcc gaucacaggg gucgcauugg    60
cgaugcucag aagcggag                                                 78

<210> SEQ ID NO 32
<211> LENGTH: 79
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 32
gggcuuguuc uggaucgcua cuuaacacac ugguaacccu cggcccuagu gucgagccag    60
gcgaugcuca gaagcggag                                                79

<210> SEQ ID NO 33
<211> LENGTH: 79
<212> TYPE: RNA
<213> ORGANISM: Artificial
<220> FEATURE:
<223> OTHER INFORMATION: synthetic construct; nucleic ac
      id having binding activity against FGF-2

<400> SEQUENCE: 33
gggcuuguuc uggaucgccc auauaggcug uuccgcggca auagaauuug caguuauugg    60
gcgaugcuca gaagcggag                                                79

<210> SEQ ID NO 34
<211> LENGTH: 78
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 34
gggcuuguuc uggaucgcua aggguuugag ucuuaucuac cugcugugca aaugcggcgg    60
cgaugcucag aagcggag                                                 78

<210> SEQ ID NO 35
<211> LENGTH: 38
<212> TYPE: RNA

```
<213> ORGANISM: Artificial
<220> FEATURE:
<223> OTHER INFORMATION: synthetic construct; nucleic acid having
      binding activity against FGF-2

<400> SEQUENCE: 35
gggaagcagg agggugacgg ugauggcagc uguuccc                              38

<210> SEQ ID NO 36
<211> LENGTH: 41
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 36
ggggcaaguu accaguguag cuaguuacua gggcgugucc c                         41

<210> SEQ ID NO 37
<211> LENGTH: 47
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 37
gggaucgcuc guugacuagg gcguacaucg ugaccagugu caguccc                   47

<210> SEQ ID NO 38
<211> LENGTH: 35
<212> TYPE: RNA
<213> ORGANISM: Artificial
<220> FEATURE:
<223> OTHER INFORMATION: synthetic construct; nucleic ac
      id having binding activity against FGF-2

<400> SEQUENCE: 38
ggguacuagg gcucuuagga gugaccagug ugccc                                35

<210> SEQ ID NO 39
<211> LENGTH: 95
<212> TYPE: DNA
<213> ORGANISM: Artificial
<220> FEATURE:
<223> OTHER INFORMATION: synthetic construct; template DNA
<220> FEATURE:
<221> NAME/KEY: misc_feature
<222> LOCATION: (36)..(75)
<223> OTHER INFORMATION: n is a, c, g, or t

<400> SEQUENCE: 39
taatacgact cactataggg cttgttctgg atcgcnnnnn nnnnnnnnnn nnnnnnnnnn     60
nnnnnnnnnn nnnnggcga tgctcagaag cggag                                 95

<210> SEQ ID NO 40
<211> LENGTH: 35
<212> TYPE: DNA
<213> ORGANISM: Artificial
<220> FEATURE:
<223> OTHER INFORMATION: synthetic construct; primer

<400> SEQUENCE: 40
taatacgact cactataggg cttgttctgg atcgc                                35
```

```
<210> SEQ ID NO 41
<211> LENGTH: 20
<212> TYPE: DNA
<213> ORGANISM: Artificial
<220> FEATURE:
<223> OTHER INFORMATION: synthetic construct; primer

<400> SEQUENCE: 41
ctccgcttct gagcatcgcc                                                    20

<210> SEQ ID NO 42
<211> LENGTH: 27
<212> TYPE: RNA
<213> ORGANISM: Artificial
<220> FEATURE:
<223> OTHER INFORMATION: synthetic construct; consensus sequence
<220> FEATURE:
<221> NAME/KEY: misc_feature
<222> LOCATION: (12)..(22)
<223> OTHER INFORMATION: n is a, c, g, or u

<400> SEQUENCE: 42
guuaccagug unnnnnnnnn nnagggc                                            27

<210> SEQ ID NO 43
<211> LENGTH: 83
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 43
gggaagaggu cagaugguuc cccgcacguu accaguguag aaaacuacua gggcguguga        60
ucacccuaug cgugcuagag uga                                                83

<210> SEQ ID NO 44
<211> LENGTH: 83
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 44
gggaagaggu cagauggccc gccucacguu accaguguga guugucacca gggcgugugu        60
ugcaccuaug cgugcuagag uga                                                83

<210> SEQ ID NO 45
<211> LENGTH: 84
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 45
gggaagaggu cagauggccu uccgcagguu accaguguag uuuaauacua gggccuguau        60
ugcaccuuau gcgugcuaga guga                                               84

<210> SEQ ID NO 46
<211> LENGTH: 100
<212> TYPE: RNA
<213> ORGANISM: Artificial
<220> FEATURE:
<223> OTHER INFORMATION: synthetic construct; nucleic acid having
``` binding activity against FGF-2

<400> SEQUENCE: 46
gggaagaggu cagauggga ccuuggcguu accaguguag gaaacuacua gggcgcgugu    60
agcaccuaug cgugcuagag ugauaugcgu gcuagaguga                        100

<210> SEQ ID NO 47
<211> LENGTH: 84
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 47
gggaagaggu cagaugguuc cccgcacguu accaguguag aaaacuacua gggcguguaa    60
ugcaccuuau gcgugcuaga guga                                          84

<210> SEQ ID NO 48
<211> LENGTH: 84
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 48
gggaagaggu cagauggcuc cccgcacgug accaguguag uuaacuacua gggcguguga    60
agcaccuauu gcgugcuaga guga                                          84

<210> SEQ ID NO 49
<211> LENGTH: 84
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 49
gggaagaggu cagaugguuc cccgcacguu accaguguag auagauacua gggcguguuu    60
agcaccuuau gcgugcuaga guga                                          84

<210> SEQ ID NO 50
<211> LENGTH: 82
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 50
gggaagaggu cagaugggcc uccacaaguu accaguguag cgcauuacua gggcuugugc    60
ucaccuaugc gugcuagagu ga                                            82

<210> SEQ ID NO 51
<211> LENGTH: 83
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 51
gggaagaggu cagauggauc ucugcacguu accaguguau guaauuacua gggcgugugu    60
ugcaccuaug cgugcuagag uga                                            83

<210> SEQ ID NO 52
<211> LENGTH: 83
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 52
gggaagaggu cagauggauc ucugcacguu accaguguaa guuguuacua gggcgugugu    60
ugcaccuaug cgugcuagag uga                                            83

<210> SEQ ID NO 53
<211> LENGTH: 83
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 53
gggaagaggu cagauggcuu ccugcacguu accauuguau guuguuacua gggcguggcu    60
ugcaccuaug cgugcuagag uga                                            83

<210> SEQ ID NO 54
<211> LENGTH: 83
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 54
gggaagaggu cagauggacu ucugcacguu accaguguag cuauuuacca gggcgugugu    60
agcaccuaug cgugcuagag uga                                            83

<210> SEQ ID NO 55
<211> LENGTH: 83
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 55
gggaagaggu cagauggaca ccugcacguu accaguguaa cuuguuacua gggcgugugu    60
agcaccuaug cgugcuagag uga                                            83

<210> SEQ ID NO 56
<211> LENGTH: 83
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 56
gggaagaggu cagauggcuu ccuacaaguu accaguguau uuaguuacua gggcuugugu    60
ggcaccuaug cgugcuagag uga                                            83

<210> SEQ ID NO 57
<211> LENGTH: 83
<212> TYPE: RNA
<213> ORGANISM: Artificial
<220> FEATURE:
<223> OTHER INFORMATION: synthetic construct; nucleic acid having
      binding activity against FGF-2

<400> SEQUENCE: 57
gggaagaggu cagauggucc ucuacagguu accaguguau uuauuuacua gggccugugu      60
ugcaccuaug cgugcuagag uga                                              83

<210> SEQ ID NO 58
<211> LENGTH: 100
<212> TYPE: DNA
<213> ORGANISM: Artificial
<220> FEATURE:
<223> OTHER INFORMATION: synthetic construct; template DNA

<400> SEQUENCE: 58
taatacgact cactataggg aagaggtcag atggggcgat gcaagttacc agtgtagcta      60
gttactaggg cgtgtgttgc ccctatgcgt gctagagtga                           100

<210> SEQ ID NO 59
<211> LENGTH: 32
<212> TYPE: DNA
<213> ORGANISM: Artificial
<220> FEATURE:
<223> OTHER INFORMATION: synthetic construct; primer

<400> SEQUENCE: 59
taatacgact cactataggg aagaggtcag at                                    32

<210> SEQ ID NO 60
<211> LENGTH: 17
<212> TYPE: DNA
<213> ORGANISM: Artificial
<220> FEATURE:
<223> OTHER INFORMATION: synthetic construct; primer

<400> SEQUENCE: 60
tcactctagc acgcata                                                     17

<210> SEQ ID NO 61
<211> LENGTH: 16
<212> TYPE: RNA
<213> ORGANISM: Artificial
<220> FEATURE:
<223> OTHER INFORMATION: synthetic construct; consensus sequence
<220> FEATURE:
<221> NAME/KEY: misc_feature
<222> LOCATION: (10)..(10)
<223> OTHER INFORMATION: n is a, c, g, or u

<400> SEQUENCE: 61
aguaguacun guuuac                                                      16

<210> SEQ ID NO 62
<211> LENGTH: 20
<212> TYPE: RNA
<213> ORGANISM: Artificial
<220> FEATURE:
<223> OTHER INFORMATION: synthetic construct; consensus sequence
<220> FEATURE:
<221> NAME/KEY: misc_feature
<222> LOCATION: (13)..(13)

```
<223> OTHER INFORMATION: n is a, c, g, or u

<400> SEQUENCE: 62
gagggugacg gungcuguuu                                                    20

<210> SEQ ID NO 63
<211> LENGTH: 11
<212> TYPE: RNA
<213> ORGANISM: Artificial
<220> FEATURE:
<223> OTHER INFORMATION: synthetic construct; consensus sequence
<220> FEATURE:
<221> NAME/KEY: misc_feature
<222> LOCATION: (7)..(7)
<223> OTHER INFORMATION: n is a, c, g, or u

<400> SEQUENCE: 63
uagggcncag u                                                             11
```